(12) United States Patent
Liu et al.

(10) Patent No.: US 7,163,799 B2
(45) Date of Patent: Jan. 16, 2007

(54) NEUROMEDIN U RECEPTOR NMUR2 AND NUCLEOTIDES ENCODING IT

(75) Inventors: Qingyun Liu, The Woodlands, TX (US); Kevin R. Lynch, Charlottesville, VA (US); Andrew D. Howard, Park Ridge, NJ (US); Theodore N. Mellin, Annadale, NJ (US); Alison Strack, Scotch Plains, NJ (US); Leonardus H. T. Van Der Ploeg, Newton, MA (US); Ruiping Wang, Maple Glen, PA (US); Qingping Jiang, Midland Park, NJ (US); David Williams, Telford, PA (US)

(73) Assignee: Merck & Co., Inc., Rahway, NJ (US)

( * ) Notice: Subject to any disclaimer, the term of this patent is extended or adjusted under 35 U.S.C. 154(b) by 275 days.

(21) Appl. No.: 10/258,423

(22) PCT Filed: Apr. 25, 2001

(86) PCT No.: PCT/US01/13386

§ 371 (c)(1),
(2), (4) Date: Apr. 8, 2003

(87) PCT Pub. No.: WO01/81418

PCT Pub. Date: Nov. 1, 2001

(65) Prior Publication Data

US 2003/0211968 A1   Nov. 13, 2003

Related U.S. Application Data

(60) Provisional application No. 60/200,718, filed on Apr. 27, 2000.

(51) Int. Cl.
  *G01N 33/53* (2006.01)
  *G01N 33/566* (2006.01)
(52) U.S. Cl. .................. 435/7.2; 435/7.21; 435/7.22; 435/7.23; 436/501
(58) Field of Classification Search .................. None
See application file for complete search history.

(56) References Cited

U.S. PATENT DOCUMENTS

| | | | | |
|---|---|---|---|---|
| 6,461,836 | B1* | 10/2002 | Elshourbagy et al. | 435/69.1 |
| 2003/0017528 | A1* | 1/2003 | Chen et al. | 435/69.1 |
| 2003/0148450 | A1* | 8/2003 | Chen et al. | 435/69.1 |

FOREIGN PATENT DOCUMENTS

| | | |
|---|---|---|
| EP | 1 255 109 | 11/2002 |
| WO | WO 00/02919 | 7/1999 |
| WO | WO 99/55732 | 11/1999 |
| WO | WO 00/22131 | 4/2000 |
| WO | WO 01/25269 | 4/2001 |
| WO | WO 01/44297 | 6/2005 |

OTHER PUBLICATIONS

Bray. (2000). Nutrition. 16, 953-960.*
Wieland et al. (2000). Expert opinion in investigational drugs. 9, 1327-1346.*
Zerangue et al (2000). Neuron. 22, 537-548.*
Appendix A. A 1-page sequence alignment.*
Sim et al.(1995). PNAS. 92, 7242-7246.*
Bray, "A Concise Review on the Therapeutics of Obesity", Nutrition, vol. 16, pp. 953-960, 2000.
Button, et al., "Aequorin-expressing mammalian cell lines used to report Ca2+ mobilization", Cell Calcium, vol. 14, pp. 663-671, 1993.
Domin, et al., "The Distribution and Biological Effects of Neuromedins B and U", Ann. NY Acad. Sci., vol. 547, pp. 391-403 (1988).
Howard, et al., "Identification of receptors for neuromedin U and its role in feeding", Nature, vol. 406, pp. 70-74, Jul. 2000.
Kojima, et al. Purification and Identification of Neuromedin U as an Endogenous Ligand or an Orphan Receptor GPR66 (FM3), Biochem and Biophys Res Comm, vol. 276, pp. 435-438, 2000).
Minamino, et al., "Neuromedin U-8 and U-25: Novel Uterus Stimulating and Hypertensive Peptides Identified in Porcine Spinal Cord", Viochem and Biophys Res Comm., vol. 130, No. 3, pp. 1078-1085, Aug. 15, 1985.
Raddatz, et al., "Identification and Characterization of Two Neuromedin U Receptors Differentially Expressed in Peripheral Tissues and the Central Nervous System", J. of Biol. Chem., vol. 275, No. 42, pp. 32452-32459, 2000.
Wieland, et al., "The role of NPY in metabolic homeostasis: implications for obesity therapy", Exp. Opin. Invest. Drugs, vol. 9, No. 6, pp. 1327-1346, 2000.
Zerangue, et al., "A New ER Trafficking Signal Regulates the Subunit Stoichiometry of Plasma Membrane KATP Channels", Neuron, vol. 22, pp. 537-548, Mar. 1999.
Appendix A, A I-Page Sequence Alignment.

* cited by examiner

*Primary Examiner*—David Romeo
*Assistant Examiner*—Steven Standley
(74) *Attorney, Agent, or Firm*—Alysia A. Finnegan; Joanne M. Giesser

(57) ABSTRACT

A new neuromedin U receptor, designated NMUR2 has been found, which is involved in modulation of feeding behavior in mammals. Ligands of this receptor are able to modulate eating, and weight gain. Amino acid sequences of the human and rat forms, as well as their nucleic acid sequences are given.

1 Claim, 21 Drawing Sheets cDNA Polynucleotide sequence of human NMUR2
(SEQ.ID.NO. 1)

```
   1 GGCTCAGCTT GAAACAGAGC CTCGTACCAG GGGAGGCTCA GGCCTTGGAT
  51 TTTAATGTCA GGGATGGAAA AACTTCAGAA TGCTTCCTGG ATCTACCAGC
 101 AGAAACTAGA AGATCCATTC CAGAAACACC TGAACAGCAC CGAGGAGTAT
 151 CTGGCCTTCC TCTGCGGACC TCGGCGCAGC CACTTCTTCC TCCCCGTGTC
 201 TGTGGTGTAT GTGCCAATTT TTGTGGTGGG GGTCATTGGC AATGTCCTGG
 251 TGTGCCTGGT GATTCTGCAG CACCAGGCTA TGAAGACGCC CACCAACTAC
 301 TACCTCTTCA GCCTGGCGGT CTCTGACCTC CTGGTCCTGC TCCTTGGAAT
 351 GCCCCTGGAG GTCTATGAGA TGTGGCGCAA CTACCCTTTC TTGTTCGGGC
 401 CCGTGGGCTG CTACTTCAAG ACGGCCCTCT TGAGACCGT GTGCTTCGCC
 451 TCCATCCTCA GCATCACCAC CGTCAGCGTG GAGCGCTACG TGGCCATCCT
 501 ACACCCGTTC CGCGCCAAAC TGCAGAGCAC CCGGCGCCGG GCCCTCAGGA
 551 TCCTCGGCAT CGTCTGGGGC TTCTCCGTGC TCTTCTCCCT GCCCAACACC
 601 AGCATCCATG GCATCAAGTT CCACTACTTC CCCAATGGGT CCCTGGTCCC
 651 AGGTTCGGCC ACCTGTACGG TCATCAAGCC CATGTGGATC TACAATTTCA
 701 TCATCCAGGT CACCTCCTTC CTATTCTACC TCCTCCCCAT GACTGTCATC
 751 AGTGTCCTCT ACTACCTCAT GGCACTCAGA CTAAAGAAAG ACAAATCTCT
 801 TGAGGCAGAT GAAGGGAATG CAAATATTCA AGACCCTGC AGAAAATCAG
 851 TCAACAAGAT GCTGTTTGTC TTGGTCTTAG TGTTTGCTAT CTGTTGGGCC
 901 CCGTTCCACA TTGACCGACT CTTCTTCAGC TTTGTGGAGG AGTGGAGTGA
 951 ATCCCTGGCT GCTGTGTTCA ACCTCGTCCA TGTGGTGTCA GGTGTCTTCT
1001 TCTACCTGAG CTCAGCTGTC AACCCCATTA TCTATAACCT ACTGTCTCGC
1051 CGCTTCCAGG CAGCATTCCA GAATGTGATC TCTTCTTTCC ACAAACAGTG
1101 GCACTCCCAG CATGACCCAC AGTTGCCACC TGCCCAGCGG AACATCTTCC
1151 TGACAGAATG CCACTTTGTG GAGCTGACCG AAGATATAGG TCCCCAATTC
1201 CCATGTCAGT CATCCATGCA CAACTCTCAC CTCCCAACAG CCCTCTCTAG
1251 TGAACAGATG TCAAGAACAA ACTATCAAAG CTTCCACTTT AACAAAACCT
1301 GAATTCTTTC AGAGCTGATC TCTCCTCTAT GCCTCAAAAC TTCA
```

FIG. 1

Predicted polypeptide sequence of human NMUR2
(SEQ.ID.NO. 2)

```
  1 MSGMEKLQNA SWIYQQKLED PFQKHLNSTE EYLAFLCGPR RSHFFLPVSV

51 VYVPIFVVGV IGNVLVCLVI LQHQAMKTPT NYYLFSLAVS DLLVLLLGMP

101 LEVYEMWRNY PFLFGPVGCY FKTALFETVC FASILSITTV SVERYVAILH

151 PFRAKLQSTR RRALRILGIV WGFSVLFSLP NTSIHGIKFH YFPNGSLVPG

201 SATCTVIKPM WIYNFIIQVT SFLFYLLPMT VISVLYYLMA LRLKKDKSLE

251 ADEGNANIQR PCRKSVNKML FVLVLVFAIC WAPFHIDRLF FSFVEEWSES

301 LAAVFNLVHV VSGVFFYLSS AVNPIIYNLL SRRFQAAFQN VISSFHKQWH

351 SQHDPQLPPA QRNIFLTECH FVELTEDIGP QFPCQSSMHN SHLPTALSSE

401 QMSRTNYQSF HFNKT
```

FIG.2

Translation of the open reading frame of human NMRU2
(SEQ.ID.NOS. 3 and 4)

```
          10                      30                      50
GGCTCAGCTTGAAACAGAGCCTCGTACCAGGGGAGGCTCAGGCCTTGGATTTTAATGTCA
                                                          MetSer 70                      90                     110
GGGATGGAAAAACTTCAGAATGCTTCCTGGATCTACCAGCAGAAACTAGAAGATCCATTC
GlyMetGluLysLeuGlnAsnAlaSerTrpIleTyrGlnGlnLysLeuGluAspProPhe 130                     150                     170
CAGAAACACCTGAACAGCACCGAGGAGTATCTGGCCTTCCTCTGCGGACCTCGGCGCAGC
GlnLysHisLeuAsnSerThrGluGluTyrLeuAlaPheLeuCysGlyProArgArgSer 190                     210                     230
CACTTCTTCCTCCCCGTGTCTGTGGTGTATGTGCCAATTTTTGTGGTGGGGGTCATTGGC
HisPhePheLeuProValSerValValTyrValProIlePheValValGlyValIleGly 250                     270                     290
AATGTCCTGGTGTGCCTGGTGATTCTGCAGCACCAGGCTATGAAGACGCCCACCAACTAC
AsnValLeuValCysLeuValIleLeuGlnHisGlnAlaMetLysThrProThrAsnTyr 310                     330                     350
TACCTCTTCAGCCTGGCGGTCTCTGACCTCCTGGTCCTGCTCCTTGGAATGCCCCTGGAG
TyrLeuPheSerLeuAlaValSerAspLeuLeuValLeuLeuLeuGlyMetProLeuGlu 370                     390                     410
GTCTATGAGATGTGGCGCAACTACCCTTTCTTGTTCGGGCCCGTGGGCTGCTACTTCAAG
ValTyrGluMetTrpArgAsnTyrProPheLeuPheGlyProValGlyCysTyrPheLys 430                     450                     470
ACGGCCCTCTTTGAGACCGTGTGCTTCGCCTCCATCCTCAGCATCACCACCGTCAGCGTG
ThrAlaLeuPheGluThrValCysPheAlaSerIleLeuSerIleThrThrValSerVal 490                     510                     530
GAGCGCTACGTGGCCATCCTACACCCGTTCCGCGCCAAACTGCAGAGCACCCGGCGCCGG
GluArgTyrValAlaIleLeuHisProPheArgAlaLysLeuGlnSerThrArgArgArg 550                     570                     590
GCCCTCAGGATCCTCGGCATCGTCTGGGGCTTCTCCGTGCTCTTCTCCCTGCCCAACACC
AlaLeuArgIleLeuGlyIleValTrpGlyPheSerValLeuPheSerLeuProAsnThr 610                     630                     650
AGCATCCATGGCATCAAGTTCCACTACTTCCCCAATGGGTCCCTGGTCCCAGGTTCGGCC
SerIleHisGlyIleLysPheHisTyrPheProAsnGlySerLeuValProGlySerAla
```

FIG.3A

```
                670                   690                   710
ACCTGTACGGTCATCAAGCCCATGTGGATCTACAATTTCATCATCCAGGTCACCTCCTTC
ThrCysThrValIleLysProMetTrpIleTyrAsnPheIleIleGlnValThrSerPhe 730                   750                   770
CTATTCTACCTCCTCCCCATGACTGTCATCAGTGTCCTCTACTACCTCATGGCACTCAGA
LeuPheTyrLeuLeuProMetThrValIleSerValLeuTyrTyrLeuMetAlaLeuArg 790                   810                   830
CTAAAGAAAGACAAATCTCTTGAGGCAGATGAAGGGAATGCAAATATTCAAAGACCCTGC
LeuLysLysAspLysSerLeuGluAlaAspGluGlyAsnAlaAsnIleGlnArgProCys 850                   870                   890
AGAAAAATCAGTCAACAAGATGCTGTTTGTCTTGGTCTTAGTGTTTGCTATCTGTTGGGCC
ArgLysSerValAsnLysMetLeuPheValLeuValLeuValPheAlaIleCysTrpAla 910                   930                   950
CCGTTCCACATTGACCGACTCTTCTTCAGCTTTGTGGAGGAGTGGAGTGAATCCCTGGCT
ProPheHisIleAspArgLeuPhePheSerPheValGluGluTrpSerGluSerLeuAla 970                   990                   1010
GCTGTGTTCAACCTCGTCCATGTGGTGTCAGGTGTCTTCTTCTACCTGAGCTCAGCTGTC
AlaValPheAsnLeuValHisValValSerGlyValPhePheTyrLeuSerSerAlaVal 1030                  1050                  1070
AACCCCATTATCTATAACCTACTGTCTCGCCGCTTCCAGGCAGCATTCCAGAATGTGATC
AsnProIleIleTyrAsnLeuLeuSerArgArgPheGlnAlaAlaPheGlnAsnValIle 1090                  1110                  1130
TCTTCTTTCCACAAACAGTGGCACTCCCAGCATGACCCACAGTTGCCACCTGCCCAGCGG
SerSerPheHisLysGlnTrpHisSerGlnHisAspProGlnLeuProProAlaGlnArg 1150                  1170                  1190
AACATCTTCCTGACAGAATGCCACTTTGTGGAGCTGACCGAAGATATAGGTCCCCAATTC
AsnIlePheLeuThrGluCysHisPheValGluLeuThrGluAspIleGlyProGlnPhe 1210                  1230                  1250
CCATGTCAGTCATCCATGCACAACTCTCACCTCCCAACAGCCCTCTCTAGTGAACAGATG
ProCysGlnSerSerMetHisAsnSerHisLeuProThrAlaLeuSerSerGluGlnMet 1270                  1290                  1310
TCAAGAACAAACTATCAAAGCTTCCACTTTAACAAAACCTGAATTCTTTCAGAGCTGATC
SerArgThrAsnTyrGlnSerPheHisPheAsnLysThr*

1330
TCTCCTCTATGCCTCAAAACTTCA
```

FIG.3B cDNA Polynucleotide Sequence of rat NMUR2
(SEQ.ID.NO. 5)

```
   1 ATGGGAAAAC TTGAAAATGC TTCCTGGATC CACGATCCAC TCATGAAGTA
  51 CTTGAACAGC ACAGAGGAGT ACTTGGCCCA CCTGTGTGGA CCCAAGCGCA
 101 GTGACCTATC CCTTCCGGTG TCTGTGGCCT ATGCGCTGAT CTTCCTGGTG
 151 GGGGTAATGG GCAATCTTCT GGTGTGCATG GTGATTGTCC GACATCAGAC
 201 TTTGAAGACA CCCACCAACT ACTATCTCTT CAGCTTGGCA GTCTCAGATC
 251 TGCTGGTCCT GCTCTTGGGG ATGCCTCTGG AAATCTACGA GATGTGGCAC
 301 AATTACCCTT TCCTGTTCGG GCCTGTGGGA TGCTACTTCA AGACAGCCCT
 351 CTTCGAGACT GTGTGCTTTG CCTCCATTCT CAGTGTCACC ACGGTTAGCG
 401 TAGAGCGCTA TGTGGCCATT GTCCACCCTT CCGAGCCAA GCTGGAGAGC
 451 ACGCGGCGAC GGGCCCTCAG GATCCTCAGC CTAGTCTGGA GCTTCTCTGT
 501 GGTCTTTTCT TTGCCCAATA CCAGCATCCA TGGCATCAAG TTCCAGCACT
 551 TTCCCAACGG GTCCTCCGTA CCTGGCTCAG CCACCTGCAC AGTCACCAAA
 601 CCCATGTGGG TGTATAACTT GATCATCCAA GCTACCAGCT TCCTCTTCTA
 651 CATCCTCCCA ATGACCCTCA TCAGCGTCCT CTACTACCTC ATGGGGCTCA
 701 GGCTGAAGAG AGATGAATCC CTTGAGGCGA ACAAAGTGGC TGTGAATATT
 751 CACAGACCCT CTAGAAAGTC AGTCACCAAG ATGCTGTTTG TCTTGGTCCT
 801 CGTGTTTGCC ATCTGCTGGA CCCCCTTCCA TGTGGACCGG CTCTTCTTCA
 851 GCTTTGTGGA AGAGTGGACA GAGTCCCTGG CTGCTGTGTT CAACCTCATC
 901 CATGTGGTAT CAGGTGTCTT CTTTTATCTG AGCTCCGCGG TCAACCCCAT
 951 TATCTATAAC CTCCTGTCTC GGCGCTTCCG GGCGGCCTTT CGAAATGTTG
1001 TCTCCCCTAC CTGCAAATGG TGCCATCCCC GGCATCGGCC ACAGGGACCT
1051 CCAGCCCAGA AGATCATCTT CTTGACAGAA TGTCACCTCG TGGAGCTGAC
1101 AGAGGATGCA GGCCCCAGT TCCCTGGTCA GTCATCCATC CACAACACCA
1151 ACCTTACCAC GGCCCCCTGT GCAGGAGAGG TACCATAA
```

FIG.4

Predicted Polypeptide Sequence of rat NMUR2
SEQ.ID.NO. 6

```
  1 MGKLENASWI HDPLMKYLNS TEEYLAHLCG PKRSDLSLPV SVAYALIFLV

51 GVMGNLLVCM VIVRHQTLKT PTNYYLFSLA VSDLLVLLLG MPLEIYEMWH

101 NYPFLFGPVG CYFKTALFET VCFASILSVT TVSVERYVAI VHPFRAKLES

151 TRRRALRILS LVWSFSVVFS LPNTSIHGIK FQHFPNGSSV PGSATCTVTK

201 PMWVYNLIIQ ATSFLFYILP MTLISVLYYL MGLRLKRDES LEANKVAVNI

251 HRPSRKSVTK MLFVLVLVFA ICWTPFHVDR LFFSFVEEWT ESLAAVFNLI

301 HVVSGVFFYL SSAVNPIIYN LLSRRFRAAF RNVVSPTCKW CHPRHRPQGP

351 PAQKIIFLTE CHLVELTEDA GPQFPGQSSI HNTNLTTAPC AGEVP
```

FIG.5

Translation of the open reading frame of rat NMUR2
(SEQ.ID.NOS.7 and 8)

```
           10                  30                  50
ATGGGAAAACTTGAAAATGCTTCCTGGATCCACGATCCACTCATGAAGTACTTGAACAGC
MetGlyLysLeuGluAsnAlaSerTrpIleHisAspProLeuMetLysTyrLeuAsnSer 70                  90                 110
ACAGAGGAGTACTTGGCCCACCTGTGTGGACCCAAGCGCAGTGACCTATCCCTTCCGGTG
ThrGluGluTyrLeuAlaHisLeuCysGlyProLysArgSerAspLeuSerLeuProVal 130                 150                 170
TCTGTGGCCTATGCGCTGATCTTCCTGGTGGGGGTAATGGGCAATCTTCTGGTGTGCATG
SerValAlaTyrAlaLeuIlePheLeuValGlyValMetGlyAsnLeuLeuValCysMet 190                 210                 230
GTGATTGTCCGACATCAGACTTTGAAGACACCCACCAACTACTATCTCTTCAGCTTGGCA
ValIleValArgHisGlnThrLeuLysThrProThrAsnTyrTyrLeuPheSerLeuAla 250                 270                 290
GTCTCAGATCTGCTGGTCCTGCTCTTGGGGATGCCTCTGGAAATCTACGAGATGTGGCAC
ValSerAspLeuLeuValLeuLeuLeuGlyMetProLeuGluIleTyrGluMetTrpHis 310                 330                 350
AATTACCCTTTCCTGTTCGGGCCTGTGGGATGCTACTTCAAGACAGCCCTCTTCGAGACT
AsnTyrProPheLeuPheGlyProValGlyCysTyrPheLysThrAlaLeuPheGluThr 370                 390                 410
GTGTGCTTTGCCTCCATTCTCAGTGTCACCACGGTTAGCGTAGAGCGCTATGTGGCCATT
ValCysPheAlaSerIleLeuSerValThrThrValSerValGluArgTyrValAlaIle 430                 450                 470
GTCCACCCTTTCCGAGCCAAGCTGGAGAGCACGCGGCGACGGGCCCTCAGGATCCTCAGC
ValHisProPheArgAlaLysLeuGluSerThrArgArgArgAlaLeuArgIleLeuSer 490                 510                 530
CTAGTCTGGAGCTTCTCTGTGGTCTTTTCTTTGCCCAATACCAGCATCCATGGCATCAAG
LeuValTrpSerPheSerValValPheSerLeuProAsnThrSerIleHisGlyIleLys
```

FIG.6A

```
                550                  570                  590
TTCCAGCACTTTCCCAACGGGTCCTCCGTACCTGGCTCAGCCACCTGCACAGTCACCAAA
PheGlnHisPheProAsnGlySerSerValProGlySerAlaThrCysThrValThrLys 610                  630                  650
CCCATGTGGGTGTATAACTTGATCATCCAAGCTACCAGCTTCCTCTTCTACATCCTCCCA
ProMetTrpValTyrAsnLeuIleIleGlnAlaThrSerPheLeuPheTyrIleLeuPro 670                  690                  710
ATGACCCTCATCAGCGTCCTCTACTACCTCATGGGGCTCAGGCTGAAGAGAGATGAATCC
MetThrLeuIleSerValLeuTyrTyrLeuMetGlyLeuArgLeuLysArgAspGluSer 730                  750                  770
CTTGAGGCGAACAAAGTGGCTGTGAATATTCACAGACCCTCTAGAAAGTCAGTCACCAAG
LeuGluAlaAsnLysValAlaValAsnIleHisArgProSerArgLysSerValThrLys 790                  810                  830
ATGCTGTTTGTCTTGGTCCTCGTGTTTGCCATCTGCTGGACCCCCTTCCATGTGGACCGG
MetLeuPheValLeuValLeuValPheAlaIleCysTrpThrProPheHisValAspArg 850                  870                  890
CTCTTCTTCAGCTTTGTGGAAGAGTGGACAGAGTCCCTGGCTGCTGTGTTCAACCTCATC
LeuPhePheSerPheValGluGluTrpThrGluSerLeuAlaAlaValPheAsnLeuIle 910                  930                  950
CATGTGGTATCAGGTGTCTTCTTTTATCTGAGCTCCGCGGTCAACCCCATTATCTATAAC
HisValValSerGlyValPhePheTyrLeuSerSerAlaValAsnProIleIleTyrAsn 970                  990                 1010
CTCCTGTCTCGGCGCTTCCGGGCGGCCTTTCGAAATGTTGTCTCCCCTACCTGCAAATGG
LeuLeuSerArgArgPheArgAlaAlaPheArgAsnValValSerProThrCysLysTrp 1030                 1050                 1070
TGCCATCCCCGGCATCGGCCACAGGGACCTCCAGCCCAGAAGATCATCTTCTTGACAGAA
CysHisProArgHisArgProGlnGlyProProAlaGlnLysIleIlePheLeuThrGlu 1090                 1110                 1130
TGTCACCTCGTGGAGCTGACAGAGGATGCAGGCCCCCAGTTCCCTGGTCAGTCATCCATC
CysHisLeuValGluLeuThrGluAspAlaGlyProGlnPheProGlyGlnSerSerIle 1150                 1170
CACAACACCAACCTTACCACGGCCCCCTGTGCAGGAGAGGTACCATAA
HisAsnThrAsnLeuThrThrAlaProCysAlaGlyGluValProEnd
```

FIG.6B

Amino-acid sequences and alignment of human, rat, and porcine NMU peptides
(SEQ.ID.NOS. 9,10,11,12)

human NMU-25          FRVDEEFQSPFASQSRGYFLFRPRN-NH$_2$
(SEQ.ID.NO. 9)

rat NMU-23            YKVNEYQGPVAPSGGFFLFRPRN-NH$_2$
(SEQ.ID.NO. 10)

porcine NMU-25        FKVDEEFQGPIASQVRRYFLFRPRN-NH$_2$
(SEQ.ID.NO. 11)

porcine NMU-8                               YFLFRPRN-NH$_2$
(SEQ.ID.NO. 12)

FIG.7

Alignment of human and rat NMUR2 polypeptide sequences
(SEQ.ID.NOS.2 and 5)

```
                  1                                                        50
human NMUR2    MEKLQNASWI YQQKLEDPFQ KHLNSTEEYL AFLCGPRRSH FFLPVSVVYV
rat NMUR2      MGKLENASWI H.....DPLM KYLNSTEEYL AHLCGPKRSD LSLPVSVAYA 51                                                       100
human NMUR2    PIFVVGVIGN VLVCLVILQH QAMKTPTNYY LFSLAVSDLL VLLLGMPLEV
rat NMUR2      LIFLVGVMGN LLVCMVIVRH QTLKTPTNYY LFSLAVSDLL VLLLGMPLEI 101                                                       150
human NMUR2    YEMWRNYPFL FGPVGCYFKT ALFETVCFAS ILSITTVSVE RYVAILHPFR
rat NMUR2      YEMWHNYPFL FGPVGCYFKT ALFETVCFAS ILSVTTVSVE RYVAIVHPFR 151                                                       200
human NMUR2    AKLQSTRRRA LRILGIVWGF SVLFSLPNTS IHGIKFHYFP NGSLVPGSAT
rat NMUR2      AKLESTRRRA LRILSLVWSF SVVFSLPNTS IHGIKFQHFP NGSSVPGSAT 201                                                       250
human NMUR2    CTVIKPMWIY NFIIQVTSFL FYLLPMTVIS VLYYLMALRL KKDKSLEADE
rat NMUR2      CTVTKPMWVY NLIIQATSFL FYILPMTLIS VLYYLMGLRL KRDESLEANK 251                                                       300
human NMUR2    GNANIQRPCR KSVNKMLFVL VLVFAICWAP FHIDRLFFSF VEEWSESLAA
rat NMUR2      VAVNIHRPSR KSVTKMLFVL VLVFAICWTP FHVDRLFFSF VEEWTESLAA 301                                                       350
human NMUR2    VFNLVHVVSG VFFYLSSAVN PIIYNLLSRR FQAAFQNVIS SFHKQWHSQH
rat NMUR2      VFNLIHVVSG VFFYLSSAVN PIIYNLLSRR FRAAFRNVVS PTCKWCHPRH 351                                                       400
human NMUR2    DPQLPPAQRN IFLTECHFVE LTEDIGPQFP CQSSMHNSHL PTALSS.EQM
rat NMUR2      RPQGPPAQKI IFLTECHLVE LTEDAGPQFP GQSSIHNTNL TTAPCAGEVP 401        413
human NMUR2    SRTNYQSFHF NKT
rat NMUR2      .......... ...
```

FIG.8

Predicted polypeptide sequences of human
NMUR2 and its transmembrane (TM) domain structure.

1 MSGMEKLQNA SWIYQQKLED PFQKHLNSTE EYLAFLCGPR RSH<u>FFLPVSV</u>

51 <u>VYVPIFVVGV IGNVLVCLVI</u> LQHQAMKTPT <u>NYYLFSLAVS DLLVLLLGMP</u>
          TM-1                                                          TM-2

101 LEVYEMWRNY PFLFGPVG<u>CY FKTALFETVC FASILSITTV SVERY</u>VAILH
                                                       TM-3

151 PFRAKLQSTR RRALR<u>ILGIV WGFSVLFSLP NTSIH</u>GIKFH YFPNGSLVPG
                                                TM-4

201 SATCTVIKPM <u>WIYNFIIQVT SFLFYLLPMT VISVLYYLMA</u> LRLKKDKSLE
                                        TM-5

251 ADEGNANIQR PCRKSVNK<u>ML FVLVLVFAIC WAPFHIDRLF FSFVEEW</u>SES
                                                    TM-6

301 LAAVFNLVH<u>V VSGVFFYLSS AVNPIIYNLL</u> SRRFQAAFQN VISSFHKQWH
                            TM-7

351 SQHDPQLPPA QRNIFLTECH FVELTEDIGP QFPCQSSMHN SHLPTALSSE

401 QMSRTNYQSF HFNKT

FIG.13

Predicted polypeptide sequences of rat NMUR2
and its transmembrane (TM) domain structure

```
  1 MGKLENASWI HDPLMKYLNS TEEYLAHLCG PKRSDLSLPV SVAYALIFLV
                                          TM-1

51 GVMGNLLVCM VIVRHQTLKT PTNYYLFSLA VSDLLVLLLG MPLEIYEMWH
                              TM-2

101 NYPFLFGPVG CYFKTALFET VCFASILSVT TVSVERYVAI VHPFRAKLES
                 TM-3

151 TRRRALRILS LVWSFSVVFS LPNTSIHGIK FQHFPNGSSV PGSATCTVTK
              TM-4

201 PMWVYNLIIQ ATSFLFYILP MTLISVLYYL MGLRLKRDES LEANKVAVNI
           TM-5

251 HRPSRKSVTK MLFVLVLVFA ICWTPFHVDR LFFSFVEEWT ESLAAVFNLI
                    TM-6

301 HVVSGVFFYL SSAVNPIIYN LLSRRFRAAF RNVVSPTCKW CHPRHRPQGP
             TM-7

351 PAQKIIFLTE CHLVELTEDA GPQFPGQSSI HNTNLTTAPC AGEVP
```

FIG.14

SEQUENCE LISTING

```
<160> NUMBER OF SEQ ID NOS: 19

<210> SEQ ID NO 1
<211> LENGTH: 1344
<212> TYPE: DNA
<213> ORGANISM: Human

<400> SEQUENCE: 1
ggctcagctt gaaacagagc ctcgtaccag gggaggctca ggccttggat tttaatgtca      60
gggatggaaa aacttcagaa tgcttcctgg atctaccagc agaaactaga agatccattc     120
cagaaacacc tgaacagcac cgaggagtat ctggccttcc tctgcggacc tcggcgcagc     180
cacttcttcc tccccgtgtc tgtggtgtat gtgccaattt ttgtggtggg ggtcattggc     240
aatgtcctgg tgtgcctggt gattctgcag caccaggcta tgaagacgcc caccaactac     300
```

```
tacctcttca gcctggcggt ctctgacctc ctggtcctgc tccttggaat gcccctggag    360
gtctatgaga tgtggcgcaa ctacccttc ttgttcgggc ccgtgggctg ctacttcaag     420
acggccctct ttgagaccgt gtgcttcgcc tccatcctca gcatcaccac cgtcagcgtg   480
gagcgctacg tggccatcct acacccgttc cgcgccaaac tgcagagcac ccggcgccgg   540
gccctcagga tcctcggcat cgtctggggc ttctccgtgc tcttctccct gcccaacacc   600
agcatccatg gcatcaagtt ccactacttc cccaatgggt ccctggtccc aggttcggcc   660
acctgtacgg tcatcaagcc catgtggatc tacaatttca tcatccaggt cacctccttc   720
ctattctacc tcctccccat gactgtcatc agtgtcctct actacctcat ggcactcaga   780
ctaaagaaag acaaatctct tgaggcagat gaagggaatg caaatattca aagaccctgc   840
agaaaatcag tcaacaagat gctgtttgtc ttggtcttag tgtttgctat ctgttgggcc   900
ccgttccaca ttgaccgact cttcttcagc tttgtggagg agtggagtga atccctggct   960
gctgtgttca acctcgtcca tgtggtgtca ggtgtcttct tctacctgag ctcagctgtc   1020
aaccccatta tctataacct actgtctcgc cgcttccagg cagcattcca gaatgtgatc   1080
tcttctttcc acaaacagtg gcactcccag catgacccac agttgccacc tgcccagcgg   1140
aacatcttcc tgacagaatg ccactttgtg gagctgaccg aagatatagg tccccaattc   1200
ccatgtcagt catccatgca caactctcac ctcccaacag ccctctctag tgaacagatg   1260
tcaagaacaa actatcaaag cttccactttt aacaaaacct gaattctttc agagctgatc   1320
tctcctctat gcctcaaaac ttca                                           1344
```

<210> SEQ ID NO 2
<211> LENGTH: 415
<212> TYPE: PRT
<213> ORGANISM: Human

<400> SEQUENCE: 2

```
Met Ser Gly Met Glu Lys Leu Gln Asn Ala Ser Trp Ile Tyr Gln Gln
  1               5                  10                  15

Lys Leu Glu Asp Pro Phe Gln Lys His Leu Asn Ser Thr Glu Glu Tyr
             20                  25                  30

Leu Ala Phe Leu Cys Gly Pro Arg Arg Ser His Phe Phe Leu Pro Val
         35                  40                  45

Ser Val Val Tyr Val Pro Ile Phe Val Val Gly Val Ile Gly Asn Val
     50                  55                  60

Leu Val Cys Leu Val Ile Leu Gln His Gln Ala Met Lys Thr Pro Thr
 65                  70                  75                  80

Asn Tyr Tyr Leu Phe Ser Leu Ala Val Ser Asp Leu Leu Val Leu Leu
                 85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175

Phe Ser Leu Pro Asn Thr Ser Ile His Gly Ile Lys Phe His Tyr Phe
            180                 185                 190
```

Pro Asn Gly Ser Leu Val Pro Gly Ser Ala Thr Cys Thr Val Ile Lys
        195                 200                 205

Pro Met Trp Ile Tyr Asn Phe Ile Ile Gln Val Thr Ser Phe Leu Phe
    210                 215                 220

Tyr Leu Leu Pro Met Thr Val Ile Ser Val Leu Tyr Tyr Leu Met Ala
225                 230                 235                 240

Leu Arg Leu Lys Lys Asp Lys Ser Leu Glu Ala Asp Glu Gly Asn Ala
                245                 250                 255

Asn Ile Gln Arg Pro Cys Arg Lys Ser Val Asn Lys Met Leu Phe Val
                260                 265                 270

Leu Val Leu Val Phe Ala Ile Cys Trp Ala Pro Phe His Ile Asp Arg
                275                 280                 285

Leu Phe Phe Ser Phe Val Glu Glu Trp Ser Glu Ser Leu Ala Ala Val
            290                 295                 300

Phe Asn Leu Val His Val Val Ser Gly Val Phe Phe Tyr Leu Ser Ser
305                 310                 315                 320

Ala Val Asn Pro Ile Ile Tyr Asn Leu Leu Ser Arg Arg Phe Gln Ala
                325                 330                 335

Ala Phe Gln Asn Val Ile Ser Ser Phe His Lys Gln Trp His Ser Gln
                340                 345                 350

His Asp Pro Gln Leu Pro Pro Ala Gln Arg Asn Ile Phe Leu Thr Glu
            355                 360                 365

Cys His Phe Val Glu Leu Thr Glu Asp Ile Gly Pro Gln Phe Pro Cys
370                 375                 380

Gln Ser Ser Met His Asn Ser His Leu Pro Thr Ala Leu Ser Ser Glu
385                 390                 395                 400

Gln Met Ser Arg Thr Asn Tyr Gln Ser Phe His Phe Asn Lys Thr
                405                 410                 415

<210> SEQ ID NO 3
<211> LENGTH: 1344
<212> TYPE: DNA
<213> ORGANISM: Human

<400> SEQUENCE: 3

```
ggctcagctt gaaacagagc ctcgtaccag gggaggctca ggccttggat tttaatgtca    60
gggatggaaa acttcagaa tgcttcctgg atctaccagc agaaactaga agatccattc    120
cagaaacacc tgaacagcac cgaggagtat ctggccttcc tctgcggacc tcggcgcagc    180
cacttcttcc tccccgtgtc tgtggtgtat gtgccaattt ttgtggtggg ggtcattggc    240
aatgtcctgg tgtgcctggt gattctgcag caccaggcta tgaagacgcc accaactac    300 tacctcttca gcctggcggt ctctgacctc ctggtcctgc tccttggaat gccctggag    360 gtctatgaga tgtggcgcaa ctaccctttc ttgttcgggc ccgtgggctg ctacttcaag    420
acggccctct ttgagaccgt gtgcttcgcc tccatcctca gcatcaccac cgtcagcgtg    480
gagcgctacg tggccatcct acacccgttc cgcgccaaac tgcagagcac ccggcgccgg    540
gccctcagga tcctcggcat cgtctgggcg ttctccgtgc tcttctccct gcccaacacc    600
agcatccatg gcatcaagtt ccactacttc cccaatgggt ccctggtccc aggttcggcc    660
acctgtacgg tcatcaagcc catgtggatc tacaatttca tcatccaggt cacctccttc    720
ctattctacc tcctcccat gactgtcatc agtgtcctct actacctcat ggcactcaga    780
ctaaagaaag acaaatctct tgaggcagat gaagggaatg caaatattca agaccctgc    840
```

-continued

```
agaaaatcag tcaacaagat gctgtttgtc ttggtcttag tgtttgctat ctgttgggcc     900
ccgttccaca ttgaccgact cttcttcagc tttgtggagg agtggagtga atccctggct     960
gctgtgttca acctcgtcca tgtggtgtca ggtgtcttct tctacctgag ctcagctgtc    1020
aaccccatta tctataacct actgtctcgc cgcttccagg cagcattcca gaatgtgatc    1080
tcttctttcc acaaacagtg gcactcccag catgacccac agttgccacc tgcccagcgg    1140
aacatcttcc tgacagaatg ccactttgtg gagctgaccg aagatatagg tccccaattc    1200
ccatgtcagt catccatgca caactctcac ctcccaacag ccctctctag tgaacagatg    1260
tcaagaacaa actatcaaag cttccacttt aacaaaacct gaattctttc agagctgatc    1320
tctcctctat gcctcaaaac ttca                                            1344
```

<210> SEQ ID NO 4
<211> LENGTH: 402
<212> TYPE: PRT
<213> ORGANISM: Human

<400> SEQUENCE: 4

```
Met Ser Gly Met Glu Lys Leu Gln Asn Ala Ser Trp Ile Tyr Gln Gln
 1               5                  10                  15

Lys Leu Glu Asp Pro Phe Gln Lys His Leu Asn Ser Thr Glu Glu Tyr
             20                  25                  30

Leu Ala Phe Leu Cys Gly Pro Arg Arg Ser His Phe Leu Pro Val
         35                  40                  45

Ser Val Val Tyr Val Pro Ile Phe Val Val Gly Val Ile Gly Asn Val
     50                  55                  60

Leu Val Cys Leu Val Ile Leu Gln His Gln Ala Met Lys Thr Pro Thr
 65                  70                  75                  80

Asn Tyr Tyr Leu Phe Ser Leu Ala Val Ser Asp Leu Leu Val Leu Leu
                 85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175

Phe Ser Leu Pro Asn Thr Ser Ile His Gly Ile Lys Phe His Tyr Phe
            180                 185                 190

Pro Asn Gly Ser Leu Val Pro Gly Ser Ala Thr Cys Thr Val Ile Lys
        195                 200                 205

Pro Met Trp Ile Tyr Asn Phe Ile Ile Gln Val Thr Ser Phe Leu Phe
    210                 215                 220

Tyr Leu Leu Pro Met Thr Val Ile Ser Val Leu Tyr Tyr Leu Met Ala
225                 230                 235                 240

Leu Arg Leu Lys Lys Asp Lys Ser Leu Glu Ala Asp Glu Gly Asn Ala
                245                 250                 255

Asn Ile Gln Arg Pro Cys Arg Lys Ser Val Asn Lys Met Leu Phe Val
            260                 265                 270

Leu Val Leu Val Phe Ala Ile Cys Trp Ala Pro Phe His Ile Asp Arg
        275                 280                 285
```

-continued

```
Leu Phe Ser Phe Val Glu Glu Trp Ser Glu Ser Leu Ala Ala Val
    290                 295                 300

Phe Asn Leu Val His Val Val Ser Gly Val Phe Phe Tyr Leu Ser Ser
305                 310                 315                 320

Ala Val Asn Pro Ile Ile Tyr Asn Leu Leu Ser Arg Arg Phe Gln Ala
                325                 330                 335

Ala Phe Gln Asn Val Ile Ser Ser Phe His Lys Gln Trp His Ser Gln
            340                 345                 350

His Asp Pro Gln Leu Pro Pro Ala Gln Arg Asn Ile Phe Leu Thr Glu
        355                 360                 365

Cys His Phe Val Glu Leu Thr Glu Asp Ile Gly Pro Gln Phe Pro Cys
    370                 375                 380

Gln Ser Ser Met His Asn Ser His Leu Pro Thr Ala Leu Ser Ser Glu
385                 390                 395                 400

Gln Met
```

<210> SEQ ID NO 5
<211> LENGTH: 1188
<212> TYPE: DNA
<213> ORGANISM: Rattus

<400> SEQUENCE: 5

| | | |
|---|---|---|
| atgggaaaac ttgaaaatgc ttcctggatc acgatccac tcatgaagta cttgaacagc | 60 |
| acagaggagt acttggccca cctgtgtgga cccaagcgca gtgacctatc ccttccggtg | 120 |
| tctgtggcct atgcgctgat cttcctggtg ggggtaatgg gcaatcttct ggtgtgcatg | 180 |
| gtgattgtcc gacatcagac tttgaagaca cccaccaact actatctctt cagcttggca | 240 |
| gtctcagatc tgctggtcct gctcttgggg atgcctctgg aaatctacga gatgtggcac | 300 |
| aattacccct tcctgttcgg gcctgtggga tgctacttca agacagccct cttcgagact | 360 |
| gtgtgctttg cctccattct cagtgtcacc acggttagcg tagagcgcta tgtggccatt | 420 |
| gtccaccctt ccgagccaa gctggagagc acgcggcgac gggccctcag gatcctcagc | 480 |
| ctagtctgga gcttctctgt ggtctttttct ttgcccaata ccagcatcca tggcatcaag | 540 |
| ttccagcact ttcccaacgg tcctccgta cctggctcag ccacctgcac agtcaccaaa | 600 |
| cccatgtggg tgtataactt gatcatccaa gctaccagct cctcttcta catcctccca | 660 |
| atgaccctca tcagcgtcct ctactacctc atggggctca ggctgaagag agatgaatcc | 720 |
| cttgaggcga acaaagtggc tgtgaatatt cacagaccct agaaagtc agtcaccaag | 780 |
| atgctgtttg tcttggtcct cgtgtttgcc atctgctgga cccccttcca tgtggaccgg | 840 |
| ctcttcttca gctttgtgga agagtggaca gagtccctgg ctgctgtgtt caacctcatc | 900 |
| catgtggtat caggtgtctt cttttatctg agctccgcgg tcaaccccat tatctataac | 960 |
| ctcctgtctc ggcgcttccg ggcggccttt cgaaatgttg tctcccctac ctgcaaatgg | 1020 |
| tgccatcccc ggcatcggcc acagggacct ccagcccaga agatcatctt cttgacagaa | 1080 |
| tgtcacctcg tggagctgac agaggatgca ggccccagt tccctggtca gtcatccatc | 1140 |
| cacaacacca accttaccac ggcccctgt gcaggagagg taccataa | 1188 |

<210> SEQ ID NO 6
<211> LENGTH: 395
<212> TYPE: PRT
<213> ORGANISM: Rattus

<400> SEQUENCE: 6

-continued

```
Met Gly Lys Leu Glu Asn Ala Ser Trp Ile His Asp Pro Leu Met Lys
 1               5                  10                  15

Tyr Leu Asn Ser Thr Glu Glu Tyr Leu Ala His Leu Cys Gly Pro Lys
                20                  25                  30

Arg Ser Asp Leu Ser Leu Pro Val Ser Val Ala Tyr Ala Leu Ile Phe
            35                  40                  45

Leu Val Gly Val Met Gly Asn Leu Leu Val Cys Met Val Ile Val Arg
 50                  55                  60

His Gln Thr Leu Lys Thr Pro Thr Asn Tyr Tyr Leu Phe Ser Leu Ala
 65                  70                  75                  80

Val Ser Asp Leu Leu Val Leu Leu Gly Met Pro Leu Glu Ile Tyr
                85                  90                  95

Glu Met Trp His Asn Tyr Pro Phe Leu Phe Gly Pro Val Gly Cys Tyr
                100                 105                 110

Phe Lys Thr Ala Leu Phe Glu Thr Val Cys Phe Ala Ser Ile Leu Ser
            115                 120                 125

Val Thr Thr Val Ser Val Glu Arg Tyr Val Ala Ile Val His Pro Phe
 130                 135                 140

Arg Ala Lys Leu Glu Ser Thr Arg Arg Ala Leu Arg Ile Leu Ser
145                 150                 155                 160

Leu Val Trp Ser Phe Ser Val Val Phe Ser Leu Pro Asn Thr Ser Ile
                165                 170                 175

His Gly Ile Lys Phe Gln His Phe Pro Asn Gly Ser Ser Val Pro Gly
                180                 185                 190

Ser Ala Thr Cys Thr Val Thr Lys Pro Met Trp Val Tyr Asn Leu Ile
            195                 200                 205

Ile Gln Ala Thr Ser Phe Leu Phe Tyr Ile Leu Pro Met Thr Leu Ile
            210                 215                 220

Ser Val Leu Tyr Tyr Leu Met Gly Leu Arg Leu Lys Arg Asp Glu Ser
225                 230                 235                 240

Leu Glu Ala Asn Lys Val Ala Val Asn Ile His Arg Pro Ser Arg Lys
                245                 250                 255

Ser Val Thr Lys Met Leu Phe Val Leu Val Leu Val Phe Ala Ile Cys
                260                 265                 270

Trp Thr Pro Phe His Val Asp Arg Leu Phe Phe Ser Phe Val Glu Glu
            275                 280                 285

Trp Thr Glu Ser Leu Ala Ala Val Phe Asn Leu Ile His Val Val Ser
            290                 295                 300

Gly Val Phe Phe Tyr Leu Ser Ser Ala Val Asn Pro Ile Ile Tyr Asn
305                 310                 315                 320

Leu Leu Ser Arg Arg Phe Arg Ala Ala Phe Arg Asn Val Val Ser Pro
                325                 330                 335

Thr Cys Lys Trp Cys His Pro Arg His Arg Pro Gln Gly Pro Pro Ala
            340                 345                 350

Gln Lys Ile Ile Phe Leu Thr Glu Cys His Leu Val Glu Leu Thr Glu
            355                 360                 365

Asp Ala Gly Pro Gln Phe Pro Gly Gln Ser Ser Ile His Asn Thr Asn
            370                 375                 380

Leu Thr Thr Ala Pro Cys Ala Gly Glu Val Pro
385                 390                 395
```

<210> SEQ ID NO 7
<211> LENGTH: 1188

<212> TYPE: DNA
<213> ORGANISM: Rattus

<400> SEQUENCE: 7

```
atgggaaaac ttgaaaatgc ttcctggatc cacgatccac tcatgaagta cttgaacagc      60
acagaggagt acttggccca cctgtgtgga cccaagcgca gtgacctatc ccttccggtg     120
tctgtggcct atgcgctgat cttcctggtg ggggtaatgg gcaatcttct ggtgtgcatg     180
gtgattgtcc gacatcagac tttgaagaca cccaccaact actatctctt cagcttggca     240
gtctcagatc tgctggtcct gctcttgggg atgcctctgg aaatctacga gatgtggcac     300
aattacccct tcctgttcgg gcctgtggga tgctacttca agacagccct cttcgagact     360
gtgtgctttg cctccattct cagtgtcacc acggttagcg tagagcgcta tgtggccatt     420
gtccacccct tccgagccaa gctggagagc acgcggcgac gggccctcag gatcctcagc     480
ctagtctgga gcttctctgt ggtctttcct ttgcccaata ccagcatcca tggcatcaag     540
ttccagcact ttcccaacgg gtcctccgta cctggctcag ccacctgcac agtcaccaaa     600
cccatgtggg tgtataactt gatcatccaa gctaccagct tcctcttcta catcctccca     660
atgaccctca tcagcgtcct ctactacctc atggggctca ggctgaagag agatgaatcc     720
cttgaggcga acaaagtggc tgtgaatatt cacagaccct ctagaaagtc agtcaccaag     780
atgctgtttg tcttggtcct cgtgtttgcc atctgctgga ccccttcca tgtggaccgg      840
ctcttcttca gctttgtgga agagtggaca gagtccctgg ctgctgtgtt caacctcatc     900
catgtggtat caggtgtctt cttttatctg agctccgcgg tcaacccat tatctataac      960
ctcctgtctc ggcgcttccg ggcggccttt cgaaatgttg tctcccctac ctgcaaatgg    1020
tgccatcccc ggcatcggcc acagggacct ccagcccaga gatcatcttc ttgacagaa     1080
tgtcacctcg tggagctgac agaggatgca ggcccccagt tccctggtca gtcatccatc    1140
cacaacacca accttaccac ggcccctgt gcaggagagg taccataa                   1188
```

<210> SEQ ID NO 8
<211> LENGTH: 396
<212> TYPE: PRT
<213> ORGANISM: Rattus

<400> SEQUENCE: 8

```
Met Gly Lys Leu Glu Asn Ala Ser Trp Ile His Asp Pro Leu Met Lys
  1               5                  10                  15

Tyr Leu Asn Ser Thr Glu Glu Tyr Leu Ala His Leu Cys Gly Pro Lys
             20                  25                  30

Arg Ser Asp Leu Ser Leu Pro Val Ser Val Ala Tyr Ala Leu Ile Phe
         35                  40                  45

Leu Val Gly Val Met Gly Asn Leu Leu Val Cys Met Val Ile Val Arg
     50                  55                  60

His Gln Thr Leu Lys Thr Pro Thr Asn Tyr Tyr Leu Phe Ser Leu Ala
 65                  70                  75                  80

Val Ser Asp Leu Leu Val Leu Leu Leu Gly Met Pro Leu Glu Ile Tyr
                 85                  90                  95

Glu Met Trp His Asn Tyr Pro Phe Leu Phe Gly Pro Val Gly Cys Tyr
            100                 105                 110

Phe Lys Thr Ala Leu Phe Glu Thr Val Cys Phe Ala Ser Ile Leu Ser
        115                 120                 125

Val Thr Thr Val Ser Val Glu Arg Tyr Val Ala Ile Val His Pro Phe
    130                 135                 140
```

-continued

```
Arg Ala Lys Leu Glu Ser Thr Arg Arg Ala Leu Arg Ile Leu Ser
145                 150                 155                 160

Leu Val Trp Ser Phe Ser Val Val Phe Ser Leu Pro Asn Thr Ser Ile
                165                 170                 175

His Gly Ile Lys Phe Gln His Phe Pro Asn Gly Ser Ser Val Pro Gly
            180                 185                 190

Ser Ala Thr Cys Thr Val Thr Lys Pro Met Trp Val Tyr Asn Leu Ile
        195                 200                 205

Ile Gln Ala Thr Ser Phe Leu Phe Tyr Ile Leu Pro Met Thr Leu Ile
    210                 215                 220

Ser Val Leu Tyr Tyr Leu Met Gly Leu Arg Leu Lys Arg Asp Glu Ser
225                 230                 235                 240

Leu Glu Ala Asn Lys Val Ala Val Asn Ile His Arg Pro Ser Arg Lys
                245                 250                 255

Ser Val Thr Lys Met Leu Phe Val Leu Val Leu Val Phe Ala Ile Cys
                260                 265                 270

Trp Thr Pro Phe His Val Asp Arg Leu Phe Phe Ser Phe Val Glu Glu
            275                 280                 285

Trp Thr Glu Ser Leu Ala Ala Val Phe Asn Leu Ile His Val Val Ser
            290                 295                 300

Gly Val Phe Phe Tyr Leu Ser Ser Ala Val Asn Pro Ile Ile Tyr Asn
305                 310                 315                 320

Leu Leu Ser Arg Arg Phe Arg Ala Ala Phe Arg Asn Val Val Ser Pro
                325                 330                 335

Thr Cys Lys Trp Cys His Pro Arg His Arg Pro Gln Gly Pro Pro Ala
            340                 345                 350

Gln Lys Ile Ile Phe Leu Thr Glu Cys His Leu Val Glu Leu Thr Glu
            355                 360                 365

Asp Ala Gly Pro Gln Phe Pro Gly Gln Ser Ser Ile His Asn Thr Asn
370                 375                 380

Leu Thr Thr Ala Pro Cys Ala Gly Glu Val Pro Glu
385                 390                 395

<210> SEQ ID NO 9
<211> LENGTH: 25
<212> TYPE: PRT
<213> ORGANISM: Human

<400> SEQUENCE: 9

Phe Arg Val Asp Glu Glu Phe Gln Ser Pro Phe Ala Ser Gln Ser Arg
1               5                   10                  15

Gly Tyr Phe Leu Phe Arg Pro Arg Asn
            20                  25

<210> SEQ ID NO 10
<211> LENGTH: 23
<212> TYPE: PRT
<213> ORGANISM: Rat

<400> SEQUENCE: 10

Tyr Lys Val Asn Glu Tyr Gln Gly Pro Val Ala Pro Ser Gly Gly Phe
1               5                   10                  15

Phe Leu Phe Arg Pro Arg Asn
            20

<210> SEQ ID NO 11
```

-continued

<211> LENGTH: 25
<212> TYPE: PRT
<213> ORGANISM: Pig

<400> SEQUENCE: 11

Phe Lys Val Asp Glu Glu Phe Gln Gly Pro Ile Ala Ser Gln Val Arg
 1               5                  10                  15
Arg Tyr Phe Leu Phe Arg Pro Arg Asn
            20                  25

<210> SEQ ID NO 12
<211> LENGTH: 8
<212> TYPE: PRT
<213> ORGANISM: Pig

<400> SEQUENCE: 12

Tyr Phe Leu Phe Arg Pro Arg Asn
 1               5

<210> SEQ ID NO 13
<211> LENGTH: 19
<212> TYPE: DNA
<213> ORGANISM: Artificial Sequence
<220> FEATURE:
<223> OTHER INFORMATION: PCR probe

<400> SEQUENCE: 13
gaaacagagc ctcgtacca                                              19

<210> SEQ ID NO 14
<211> LENGTH: 33
<212> TYPE: DNA
<213> ORGANISM: Artificial Sequence
<220> FEATURE:
<223> OTHER INFORMATION: PCR probe

<400> SEQUENCE: 14
agtcggatcc aattcaggtt ttgttaaagt gga                              33

<210> SEQ ID NO 15
<211> LENGTH: 20
<212> TYPE: DNA
<213> ORGANISM: Artificial Sequence
<220> FEATURE:
<223> OTHER INFORMATION: PCR probe
<220> FEATURE:
<221> NAME/KEY: misc_feature
<222> LOCATION: (1)...(20)
<223> OTHER INFORMATION: n = A,T,C or G

<400> SEQUENCE: 15
ttcagcctgg cngtntcnga                                             20

<210> SEQ ID NO 16
<211> LENGTH: 21
<212> TYPE: DNA
<213> ORGANISM: Artificial Sequence
<220> FEATURE:
<223> OTHER INFORMATION: PCR probe
<220> FEATURE:
<221> NAME/KEY: misc_feature
<222> LOCATION: (1)...(21)
<223> OTHER INFORMATION: n = A,T,C or G

<400> SEQUENCE: 16
gctgaggatn gangcraarc a                                           21

```
<210> SEQ ID NO 17
<211> LENGTH: 45
<212> TYPE: DNA
<213> ORGANISM: Artificial Sequence
<220> FEATURE:
<223> OTHER INFORMATION: PCR probe

<400> SEQUENCE: 17
aggaaagggt aattgtgcca catctcgtag atttccagag gcatc          45

<210> SEQ ID NO 18
<211> LENGTH: 43
<212> TYPE: DNA
<213> ORGANISM: Artificial Sequence
<220> FEATURE:
<223> OTHER INFORMATION: PCR probe

<400> SEQUENCE: 18
cacagtctcg aagagggctg tcttgaagta gcatcccaca ggc            43

<210> SEQ ID NO 19
<211> LENGTH: 45
<212> TYPE: DNA
<213> ORGANISM: Artificial Sequence
<220> FEATURE:
<223> OTHER INFORMATION: Probe

<400> SEQUENCE: 19
ttctggtggt aatctttgag gcgatattgg cgtacctctg caagc          45
```

NEUROMEDIN U RECEPTOR NMUR2 AND NUCLEOTIDES ENCODING IT

CROSS-REFERENCE TO RELATED APPLICATIONS

This application is a § 371 National Stage Application of PCT/US01/13386, international filing date of Apr. 25, 2001, which claims priority to U.S. Ser. No. 60/200,718, filed Apr. 27, 2000, now expired.

FIELD OF THE INVENTION

This invention relates to new human and rat neuromedin U receptors, designated hNMUR2, and rNMUR2, to nucleic acids encoding them, and to use of them in various assays.

BACKGROUND OF THE INVENTION

Neuromedin U (NMU) is a neuropeptide that is widely distributed in the gut and central nervous system, particularly in brain regions implicated in the control of feeding behavior. NMU belongs to the broad class of neuropeptides first isolated from porcine spinal cord and later from other species with potent activity on smooth muscle. One orphan receptor designated FM-3 (now NMUR1) was previously identified as a high affinity receptor of NMU, which is the subject of U.S. Provisional Patent Application Ser. No. 60/092,623 (filed Jul. 13, 1998) and International Patent Application No. PCT/US99/15941 (filed Jul. 13, 1999). NMU, when injected into the rat brain, caused a marked suppression of food intake. Thus it appears that ligands of neuromedin receptors have potential as drugs which modulate feeding and regulate weight. However, it is equally clear that NMUR1 is not the only receptor whose activity is responsible for eating behaviors.

It would be desirable to further identify and characterize other receptors whose ligands are potential drugs for eating disorders.

DETAILED DESCRIPTION OF THE INVENTION

One aspect of this invention is a novel human receptor, designated hNMUR2 (SEQ.ID.NO. 2), free from associated proteins. This invention also relates to various functional domains of this receptor, such as the extracellular domain and the intracellular domain, and to hybrid molecules comprising at least one of these sequences. Also part of this invention are nucleic acids which encode this receptor, vectors such as viral vectors, plasmids and the like, which comprise these nucleic acid sequences, and host cells which comprise the vectors. In preferred embodiments, the nucleic acid is DNA, and especially cDNA.

Another aspect of this invention a method to identify compounds which modulate the feeding activity of a mammal comprising:
contacting the compound and a NMUR2 receptor; and
determining if activity of the NMUR2 receptor is modulated.

Another aspect of this invention is the rat homologue of the human receptor (designated rNMUR2), which is free from associated proteins (SEQ.ID.NO. 6.). This invention also relates to various functional domains of this receptor, such as the extracellular domain and the intracellular domain, and to hybrid molecules comprising at least one of these sequences. Another aspect of this invention is a nucleic acid which encodes the rNMUR2 receptor; in preferred embodiments the nucleic acid is DNA, and is preferably cDNA. Yet another aspect of this invention are vectors, such as plasmids, viral vectors, and the like which comprise a rNMUR2 gene. Still another aspect of this invention are host cells which comprise a vector carrying a rNMUR2 gene.

DESCRIPTION OF THE FIGURES

FIG. 1 is the cDNA sequence of human NMUR2 (SEQ.ID.NO. 1).

FIG. 2 is the predicted polypeptide sequence of human NMUR2 (SEQ. ID. NO. 2).

FIG. 3 is the translation of the open reading frame of human NMUR2 (SEQ.ID.NOS. 3 and 4).

FIG. 4 is the cDNA sequence of rat NMUR2 (SEQ.ID.NO. 5)

FIG. 5 is the predicted polypeptide sequence of rat NMUR2 (SEQ.ID.NO. 6).

FIG. 6 is the translation of the open reading frame of rat NMUR2 (SEQ.ID.NOS. 7 and 8).

FIG. 7 is the amino acid sequences and alignments of human, rat and porcine neuromedin U (SEQ.ID.NOS. 9, 10, 11, and 12)

FIG. 8 shows the alignment of human NMUR2 protein and rat NMR2 protein.

FIG. 9A is NMUR2 in the aequorin assay using HEK293/aeq17 cells transiently transfected with human NMUR2. FIG. 9B is NMUR2 in the FLIPR assay using COS-7 cells transiently transfected with human NMUR2. In the FLIPR assay, total fluorescence was normalized to the maximum amount of fluorescence detected in the presence of the calcium ionophore A23187. (▼) porcine NMU-8; (■) human NMU-25; (▲) rat NMU-23; (♦) porcine NMU-25. All the assays are shown as the means (+/−SEM) of triplicate determinations.

FIG. 11A shows localization of NMU mRNA in coronal brain sections using $^{33}$P-labeled anti-sense oligonucleotide probe specific for the gene encoding NMU. ARC: arcuate nucleus; ME: median eminence. The signals were completely blocked in the presence of 100-fold molar excess of unlabeled probe. FIG. 11B shows a decrease of NMU mRNA in the ventromedial hypothalamic area in rats fasted for 48 hours. Data shown are means (±SEM) of three experiments. *$P<0.05$, student t test.

FIG. 12A shows the effect on overnight food intake. Food intake, expressed as percentage of control group, was significantly decreased in rats injected with 3 μg (−38±6%, n=12 per group) and 10 μg (−32±3%, n=12 per group) of NMU (ANOVA, F(3) 8.4, P=0.0002), and in rats injected with the positive control melanocortin agonist MT-II (0.3 μg; t(28)10.2, $P<0.01$).  Scheffe post hoc analysis, $P<0.01$. FIG. 12B shows effect on cumulative feeding duration. Feeding duration was significantly decreased in rats injected with NMU either at 3 μg (−33%) or 10 μg (−39%) or with the positive control MT-II (−71%). FIG. 12C is core temperature change. A transient increase in core temperature was seen in the 3 μg NMU group that started about 40 min. post-dosing and lasted for approximately one hour. FIG. 12D is change in gross motor activity in rats in the fist hour post dosing. Activity was measured for 24 hours after NMU administration and compared to those of the same period of the pre-treatment. Gross motor activity was increased only in the first hour post-dosing and then returned to their pre-treatment levels in rats injected with either 1 or 3 μg of NMU. , P<0.02. FIG. 12E is taste aversion. NMU at either 3 or 10 μg did not decrease saccharin intake relative to total intake at 24 hours post-dosing in a conditioned taste aversion assay. LiCl, an emetic control, decreased saccharin intake. [t test: t(6) 3.2, , P=0.02]. FIG. 12F is sodium appetite. NMU at either 3 or 10 μg did not significantly change the total amount of salt intake while LiCl significantly decreased salt intake. [t test: t(4) 5.0, , P=0.008].

FIG. 13 shows the various domains of human NMUR2 (SEQ.ID.NO. 2). The seven transmembrane domains (TM 1–7) are underlined. The sequence upstream of TM-1 is an extracellular domain, while sequences downstream of TM-7 is an intracellular domain.

FIG. 14 shows the various domains of rat NMUR2 (SEQ.ID.NO. 6). The seven transmembrane domains (TM 1–7) are underlined. The sequence upstream of TM-1 is an extracellular domain, while sequences downstream of TM-7 is an intracellular domain.

Figure 9A:
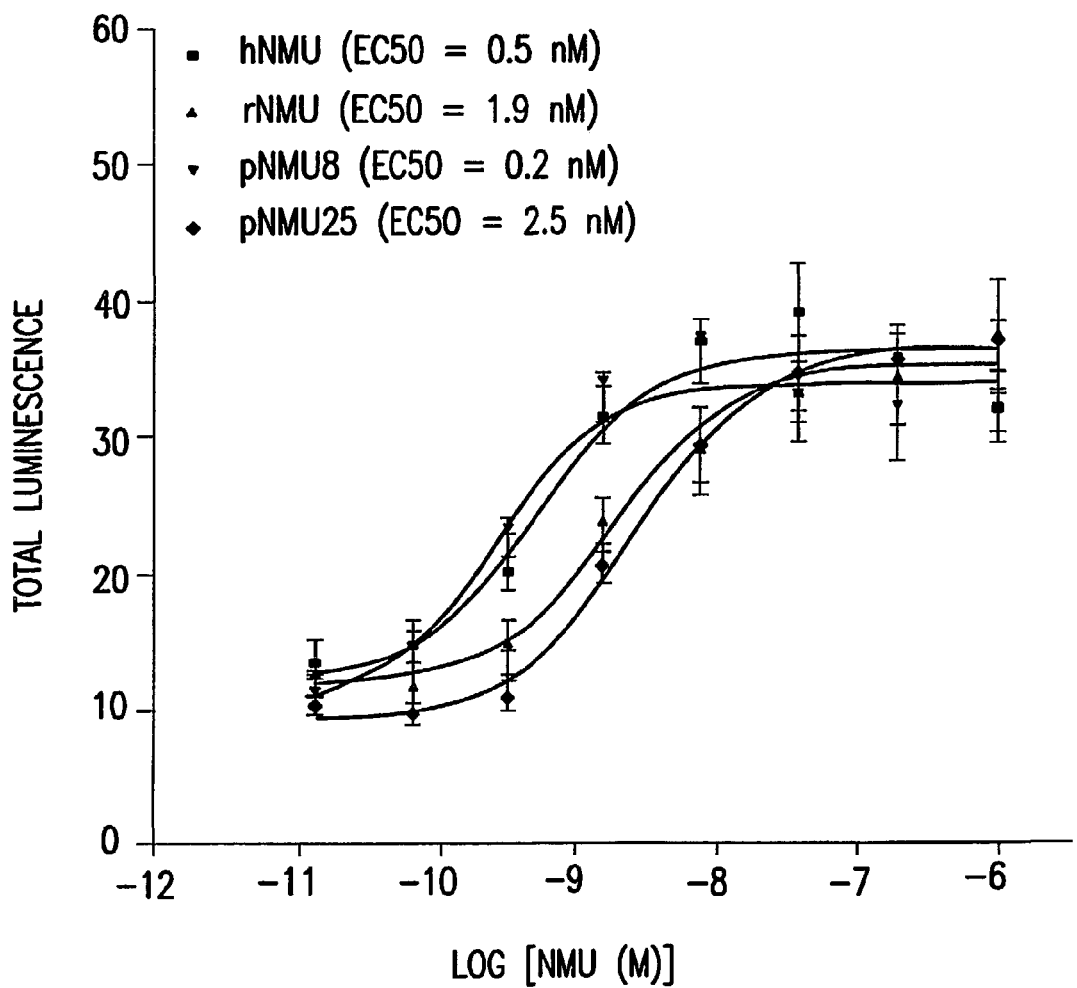
FIGS. 9A and 9B show functional activation of NMUR2 by NMU.

As used within the specification and claims the following definitions apply:

FM-3 (also designated NMUR1) is a previously identified human neuromedin U receptor, subject of U.S. Provisional Patent Application Ser. No. 60/092,623 (filed Jul. 13, 1998) and International Patent Application No. PCT/US99/15941 (filed Jul. 13, 1999).

NMUR2 (also designated FM-4) is a second neuromedin U receptor which plays a role in modulating the feeding behavior of a mammal. As used throughout "NMUR2" is not meant to refer to any particular origin of the NMUR2. "hNMUR2" means human NMUR2; "rNMUR2" means rat NMUR2.

NMU means neuromedin U.

"Free from associated protein" means that the receptor is not a naturally occurring NMUR2 receptor bound to its natural cell membrane.

A gene sequence and deduced amino acid sequence of a human orphan receptor was disclosed in WO 99/55732, published Nov. 4, 1999 (assigned to Astra Pharma, Inc.), and hereby incorporated by reference. Based on its structural similarity to the neurotensin receptor, this orphan receptor was designated NLR (neurotensin-like receptor), and it was hypothesized that its ligands would be useful agents for producing anesthesia and analgesia. The receptors of this invention share some gross structural similarity to the NLR receptor—both are the same length, but the human NMUR2 has six amino acids which differ from the NLR receptor:

| Amino Acid Position | NLR | NMUR2 |
|---|---|---|
| 271 | Leucine | Phenylalanine |
| 298 | Threonine | Serine |
| 315 | Leucine | Phenylalanine |
| 371 | Serine | Phenylalanine |
| 383 | Leucine | Proline |
| 388 | Valine | Methionine |

These six amino acid differences may contribute to NMR2's different activity. NMUR2 is involved with modulation of feeding behavior rather than anesthesia and analgesia.

Thus, one aspect of this invention is a method for identifying a compound which modulates feeding activity or weight of a mammal comprising:

a) contacting a cell comprising NMUR2 with the compound;

b) determining if the compound modulates NMUR2 activity.

Preferably the NMUR2 is recombinantly expressed in the cell. It may be introduced into the cell by conventional genetic engineering techniques, such as by conventional vectors including plasmids. Alternatively a cell line may be created which expresses NMUR2 in a non-transient fashion. Any host cell which is convenient may be used in these assays, preferably a human cell when the NMUR2 is the human NMUR2. Examples of suitable cell lines include 293 cells.

NMUR2 activity modulation can be determined in a number of ways. It may be a qualitative determination, i.e. a "positive" verses "negative" response. Alternately, the modulation can be quantified. Control systems may also be used, such as cells which are either mock-transfected and exposed to the putative ligand, or NMUR2 transfected cells which are exposed to a known negative or positive ligand.

In general, modulation of a receptor activity may be determined using a transactivation assay. In this assay, a "reporter construct" is introduced into a cell, which expresses either a recombinant receptor, or an endogenous receptor. The reporter construct comprises a reporter gene encoding a protein whose transcription and/or translation is easily measured, including such genes as β-galactosidase, luciferase, aequolorin, CAT, and the like. Upstream is a promoter (either the promoter naturally associated with the reporter gene, or a heterologous promoter) and upstream of the promoter is an activation sequence. When a ligand binds to the receptor, a cascade of intracellular reactions occur, and the result is that a binding protein binds to the activation sequence, activating the promoter, and transcription and translation of the reporter gene occurs. Such assays are described in U.S. Pat. No. 5,401,629, which is hereby incorporated by reference.

The cell line used in this assay is preferably a mammalian cell line, more preferably a human cell line. In one preferred embodiment the cell line is HEK293/aeq17, a human embryonic kidney cell line which contains an aqueorlin reporter gene. It is described in Button et al 1993 *Cell Calcium* 14:663–671, which is hereby incorporated by reference.

Another assay which is part of this invention is a FLIPR (Fluorometric Imaging Plate Reader) assay which monitors changes of intracellular $Ca^{2+}$ concentration in real time. Thus another aspect of this invention is a method of identifying compounds which modulate the feeding behavior of an individual comprising: contacting cells expressing NMUR2 receptors with a compound; and determining changes in intracellular $Ca^{+2}$ concentration. In these assays, human, porcine and rat NMU activated NMUR2 with high affinity, and lead to $Ca^{+2}$ mobilization.

Another assay contemplated by this invention is a method of identifying compounds which modulate feeding behavior in an individual by a) contacting the compound and a NMUR2, and determining if binding occurs. In these assays, whole cells expressing the NMUR2 receptor are not necessary. While they can be used, membrane preparations, lysed cells or any other preparation containing receptors will suffice. Binding may be determined by monitoring behavior of a labeled ligand, such as $^{125}$I-NMU-23 or appropriately labeled compound.

Rat NMUR2

Another aspect of this invention is the rat homologue of human NMUR2, and nucleic acids encoding this sequence. Rat NMUR2 was isolated using degenerate PCR on rat genomic DNA followed by genomic walking and PCR from rat cDNA. The rat gene was identified in genomic DNA. The open reading frame of rat NMUR2 encodes a protein of 395 amino acids, and is approximately 80% identical to the human NMUR2. The rNMUR2 can be used in assays in the same was as hNMUR2.

Another aspect of this invention are active fragments of NMUR2. These proteins are G-coupled proteins, exhibiting the classic 7-transmembrane domain structure (see FIGS. 13 and 14). Thus this invention includes active fragments, such as the extracellular domain which contains the binding region, which may, alone be used in binding assays for ligands, or which may be coupled to at least one domain from another receptor, creating a hybrid receptor. Additionally hybrid receptors can be created which utilize the intracellular domain on NMUR2 and at least one other region from a different receptor. Hybrids between the rat/human sequences are also included as part of this invention.

The following non-limiting Examples are presented to better illustrate the invention.

EXAMPLES

Example 1

Cloning of Human NMUR2

Genbank sequences were searched for sequences potentially encoding novel G protein-coupled receptors using the FAST_PAN data display tool (Retief, J.et al 1999 *Genome Res* 9:373–382, which is hereby incorporated by reference). The genomic sequence AC008571 (Genbank accession number) contained a putative gene, preliminarily termed FM-4 that is approximately 51% identical to NMUR1 (both of which are hereby incorporated by reference).

Two primers, FM-4.F1 (5'-GAA ACA GAG CCT CGT ACC A-3') (SEQ.ID.NO. 13) and FM-4.R1 (AGT CGG ATC CAA TTC AGG TTT TGT TAA AGT GGA) (SEQ.ID.NO. 14) were synthesized and used to amplify the full-length coding sequence of FM-4 from human testis cDNA. The PCR product was cloned into the vector pCRII (Invitrogen, Inc.), sequenced, and subcloned into the mammalian expression vector pcDNA3.1(–) (Invitrogen, Inc.). It was subsequently renamed NMUR2.

Example 2

Isolation of Rat Orthologs of NMUR2

For the isolation of rat NMUR2, two degenerate primers (forward): 5'-TTC AGC CTG GCN GTN TCN GA-3' (SEQ.ID.NO. 15) and (reverse): 5'-GCT GAG GAT NGA NGC RAA RCA-3' (SEQ.ID.NO. 16) were used to carry out PCR reactions on rat genoric DNA. The resulting PCR product was subdloned into pCRII and four independent clones were sequenced. Specific primers were synthesized and used to carry out genomic walking. Sequences corresponding to the start and stop codons of human NMUR2 were identified, and PCR primers flanking the coding sequence were used to amplify the full-length open reading from rat stomach cDNA. The PCR product was cloned into pCRII and sequenced.

Example 3

Generation of NMUR2-Expressing Cells

The complete coding sequence of hNMUR2 was subcloned into the expression vector pIRESpuromycin (Clontech, Inc., Palo Alto, Calif., USA). The plasmid hFM4/pIRESpuro was then transfected into HEK293/aeq17 cells (Button and Brownstein, 1993, *Cell Calcium*, 14:663–671) using Lipofectamine-2000 (Gaithersburg, Md., USA) and cells stable expressing hFM-4 were selected as described in Liu et al, 1999 *Biochem. Biophys. Res. Commun.* 266: 174–178, which is hereby incorporated by reference.

Example 4

Aequorin Functional Assays

The HEK293/aeq17 cell line was licensed from NIH (Button and Brownstein, 1993, *Cell Calcium*, 14:663–671). The cells were grown in Dulbecco's Modified Medium (DMEM, GIBCO-BRL, Gaithersburg, Md., USA)+10% fetal bovine serum (heat inactivated), 1 mM sodium pyruvate, 500 µg/ml Geneticin, 100 µg/ml streptomycin, and 100 units/ml penicillin. NMUR2/pIRESpuro plasmid DNA was transiently transfected into HEK293/aeq17 using Lipofectamine-2000 (Gaithersburg, Md., USA) following the conditions suggested by GIBCO-BRL. Twenty four hours after transfection, cells were washed once with DMEM+ 0.1% fetal bovine serum, and then charged for one hour at 37° C./5% $CO_2$ in DMEM containing 8 µM coelenterazine cp (Molecular Probes, Eugene, Oreg., USA) and 30 µM glutathione. The cells were then washed once with Versene (GIBCO-BRL, Gaithersburg, Md., USA), detached using Enzyme-free cell dissociation buffer (GIBCO-BRL, Gaithersburg, Md., USA), diluted into ECB (Ham's F12 nutrient mixture (GIBCO-BRL)+0.3 mM $CaCl_2$, 25 mM HEPES, pH7.3, 0.1% fetal bovine serum). The cell suspension was centrifuged at 500×g for 5 min. The supernatant was removed, and the pellet was then resuspended in 10 mL ECB. The cell density was determined by counting with a hemacytometer and adjusted to 500,000 cells/ml in ECB.

Human NMU-25 was custom synthesized by Research Genetics (Huntsville, Ala., USA). Rat NMU-23, porcine NMU-8, and porcine NMU-25 were purchased from Phoenix Pharmaceuticals (Belmont, Calif., USA). Results are shown in FIG. 9A.

Example 5

FLIPR Functional Assay

Figure 9B:
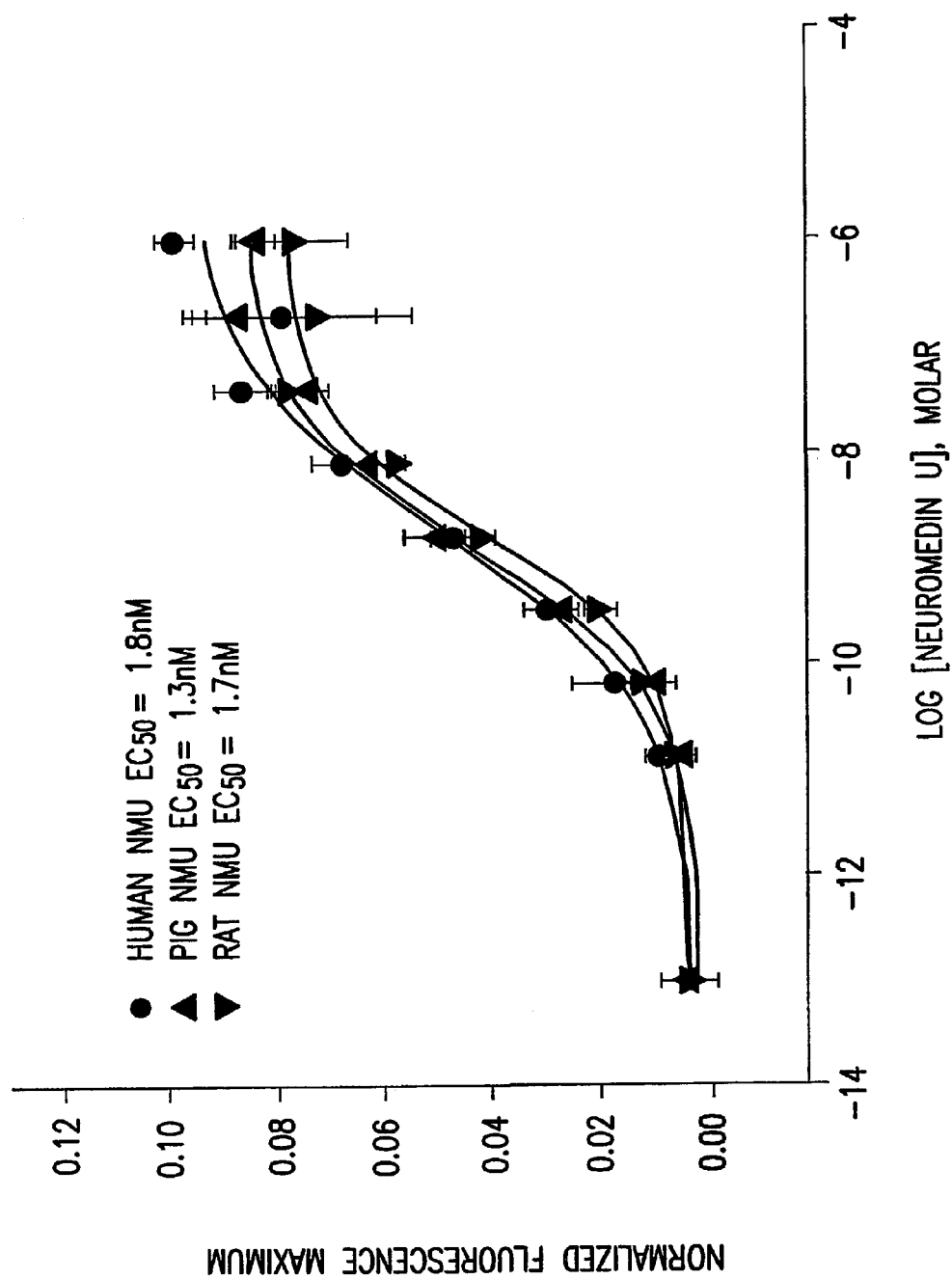
Figure 10A:
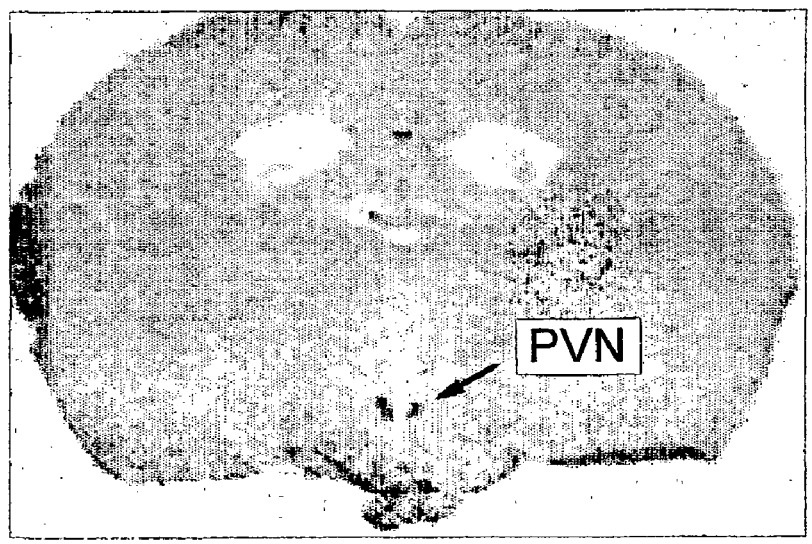
FIGS. 10A and 10B are in situ hybridization analysis of NMUR2 in the rat brain using $^{33}$P-labeled anti-sense oligonucleotide probe specific for rat NMUR2, showing specific expression of NMUR2 in the PVN (paraventricular nucleus of the hypothalamus), Ep (ependymal layer in the wall of the third ventricle), and CA1 layer of the hippocampus. The signals were completely blocked in the presence of 100-fold molar excess of unlabeled probe.
Figure 10B:
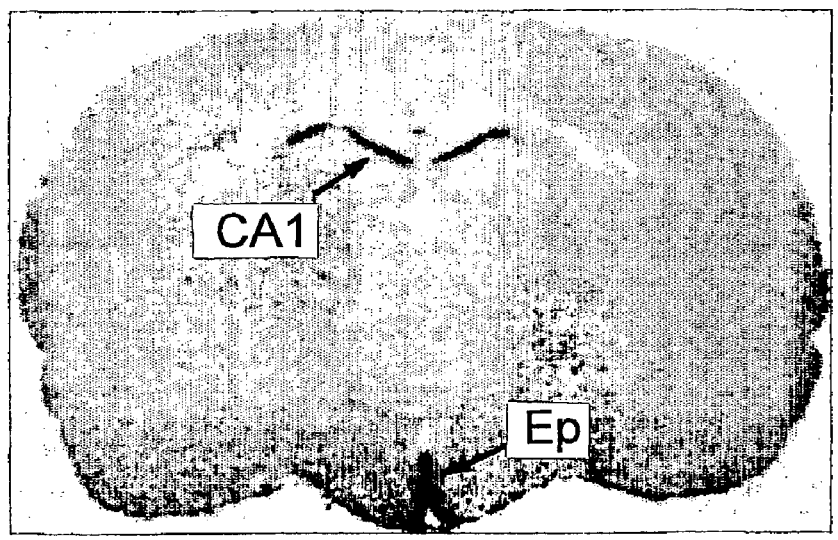
Figure 11A:
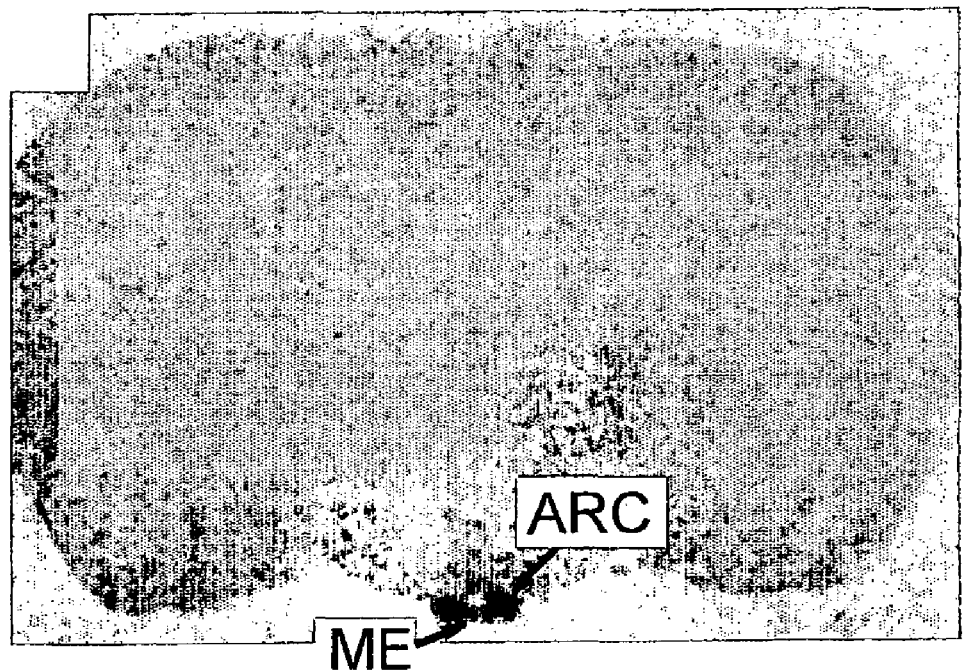
FIGS. 11A and 11B are in situ hybridization analysis of NMU in the rat brain.
Figure 11B:
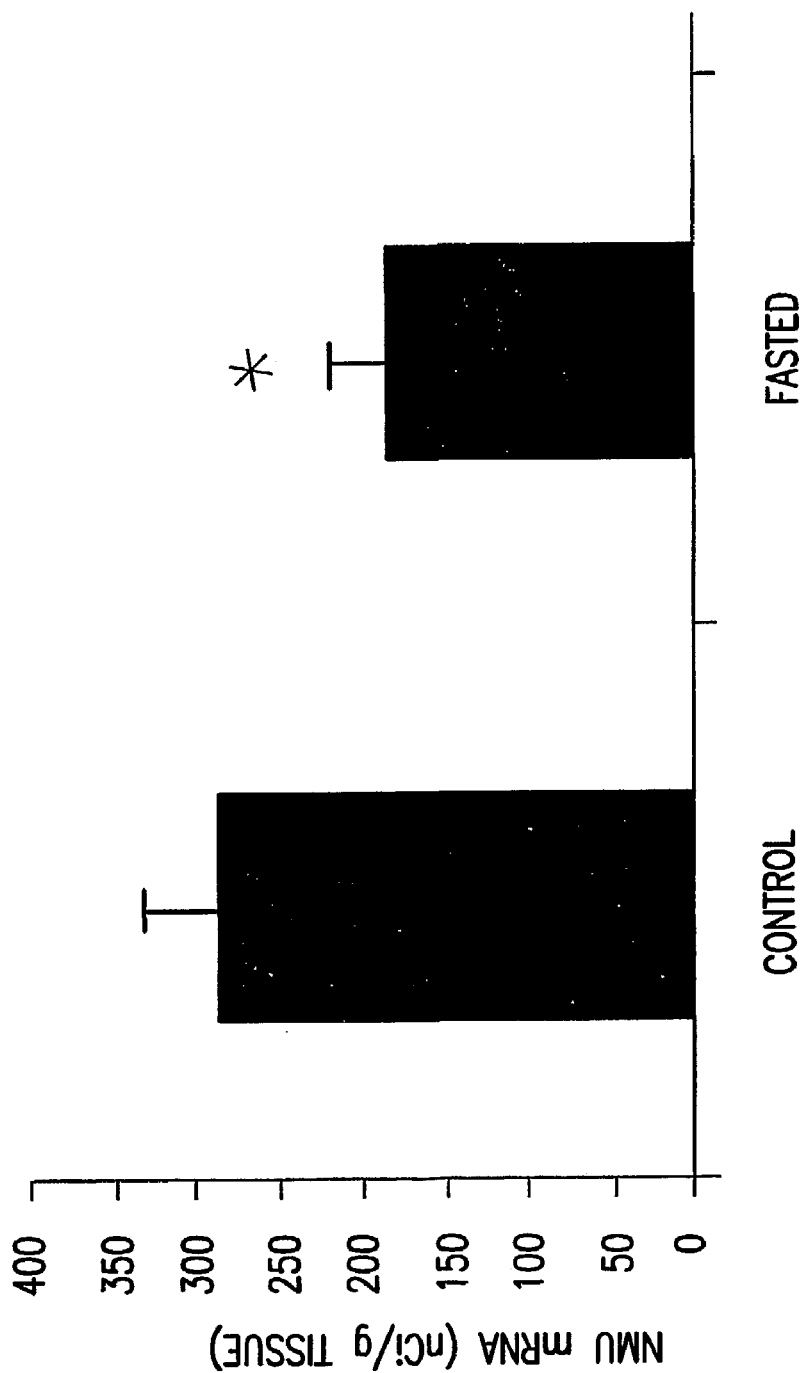
Figure 12A:
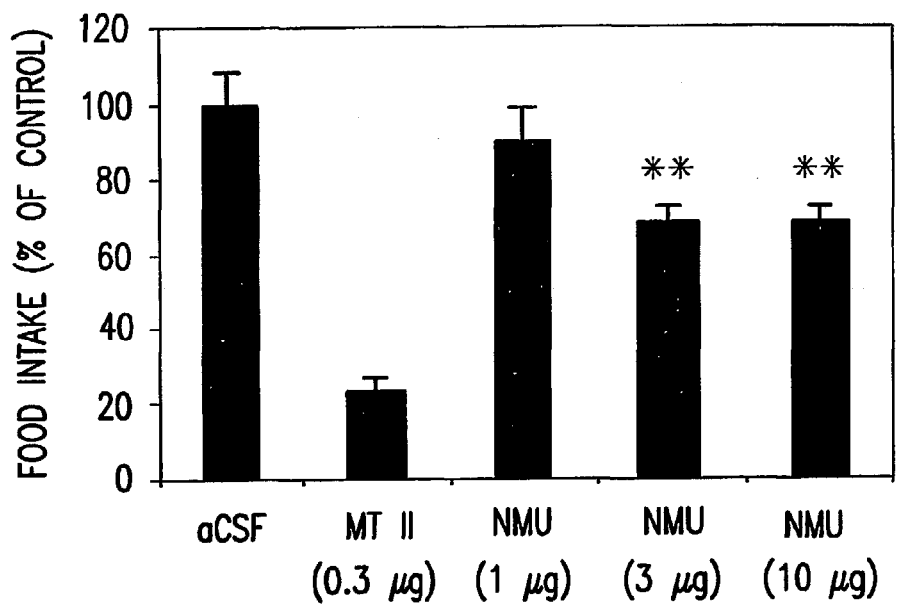
FIGS. 12A–F show the effect of ICV-administrated NMU on food intake and other behaviors in rats.
Figure 12B:
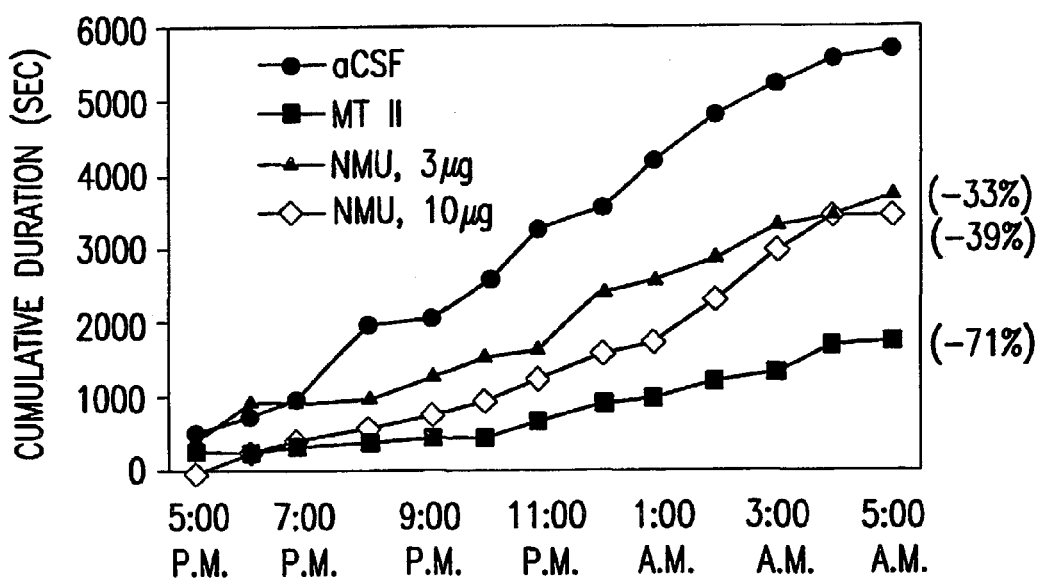
Figure 12C:
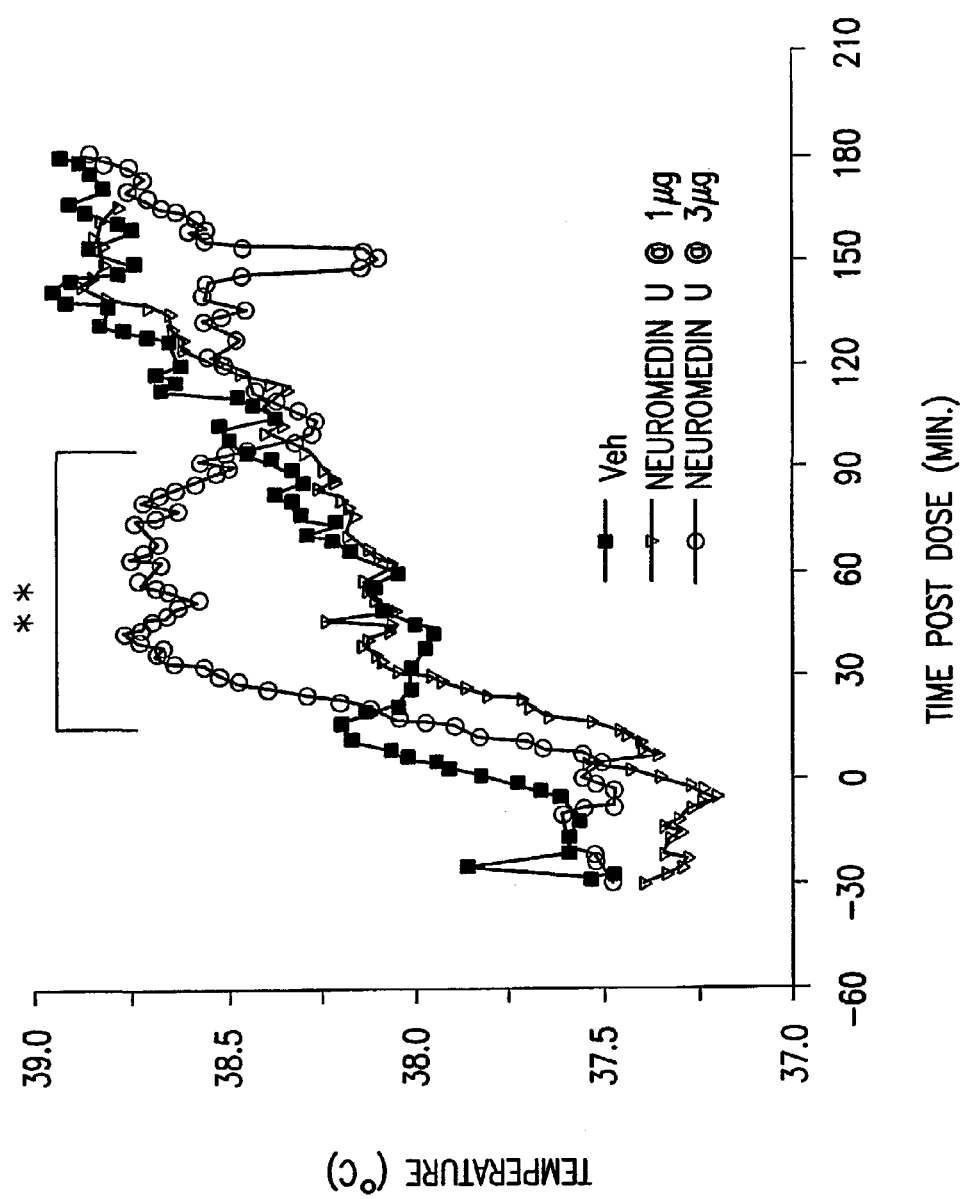
Figure 12D:
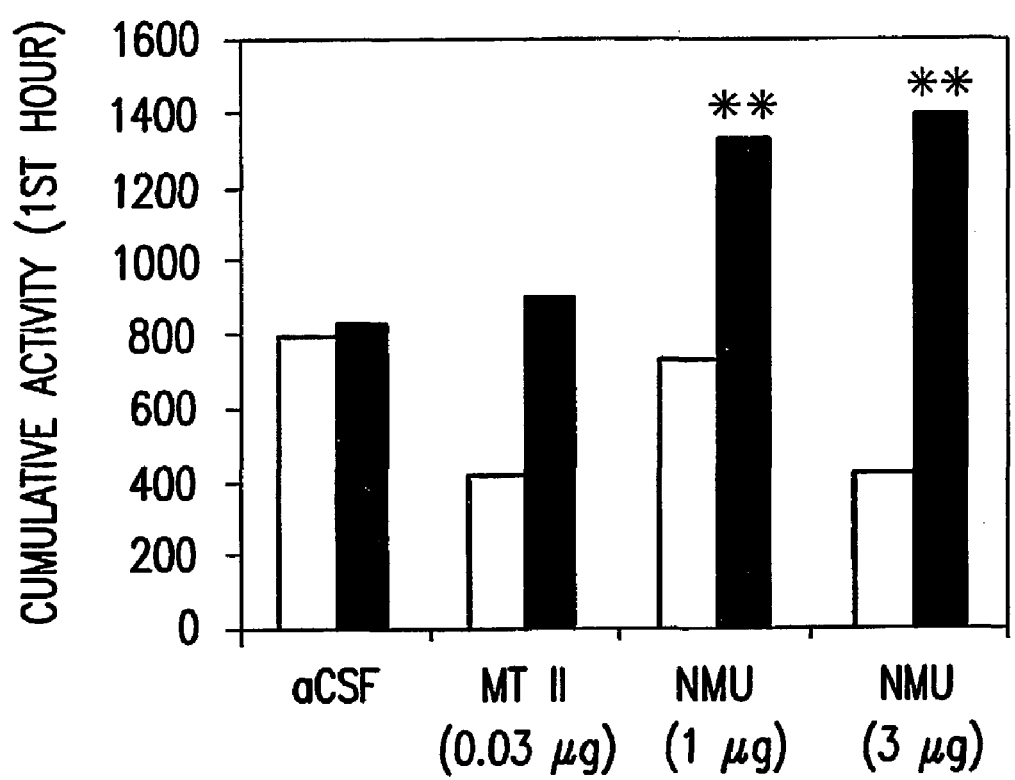
Figure 12E:
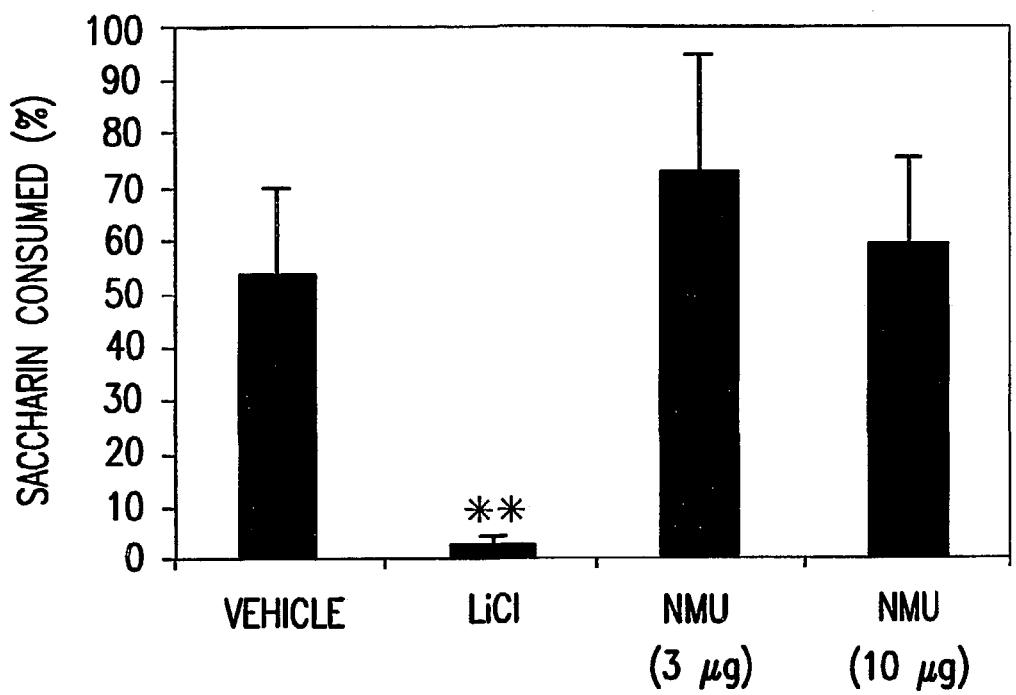
Figure 12F:
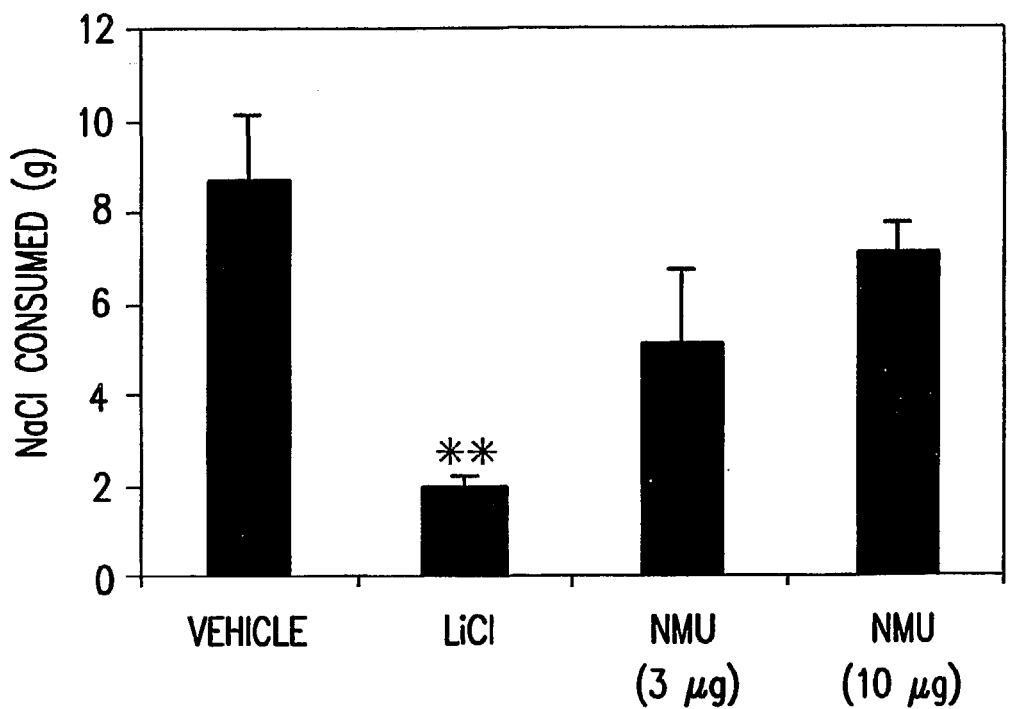

Cos-7 cells, grown in Dulbecco's Modified Medium (DMEM, GIBCO-BRL, Gaithersburg, Md., USA)+10% fetal bovine serum, were transfected with h NMUR2/pcDNA3.1 using Lipofectamine-2000 (GIBCO-BRL, Gaithersburg, Md., USA). Two days post transfection, the cells were detached and seeded into 96-well plates at approximately 10,000 cells/well. The next day, cells were loaded with Fluo-3 in the presence of 2.5 mM probenicid. After washing, the cells were treated with varying concentrations of NMU. Fluorescence output was measured by a Fluorometric Imaging Plate Reader (FLIPR, Molecular Devices, Inc.). Results are shown in FIG. 9B.

Example 6

Expression Analysis

Quantitative in situ hybridization analysis in the rat brain was carried out described previously (Guan, X. M.,et al,.1998. *Brain Res Mol Brain Res* 59, 273–279, which is hereby incorporated by reference). For rNMUR2, the probe used was $^{33}$P-labeled anti-sense oligonucleotides (equal mix of oligo 420: 5'-AGG AAA GGG TAA TTG TGC CAC ATC TCG TAG ATT TCC AGA GGC ATC-3'(SEQ.ID. NO.17) and oligo 421: 5'-CAC AGT CTC GAA GAG GGC TGT CTT GAA GTA GCA TCC CAC AGG C-3'(SEQ.ID.NO.18)). For NMU, the probe used was $^{33}$P-labeled anti-sense oligonucleotide: 5'-TTC TGG TGG TAA TCT TTG AGG CGA TAT TGG CGT ACC TCT GCA AGC-3' (SEQ.ID.NO.19). Results are shown in FIGS. 10A, 10B, 11A and 11B.

Example 7

Animal Studies

Male rats (Charles River Sprague Dawley) weighing 250–350 g were maintained in a temperature and humidity controlled facility with a 12 hour light/dark cycle (4:00 AM lights on). Rats were individually housed in custom designed shoebox cages on wire floors and fed ad libitum with fresh diet provided daily. The shoebox cage had an external, restricted access feeder assembly that allows the animal to place only its head through an opening in the feeder assembly to access a detachable clear plastic food drawer. Attached to the food drawers was an infrared feeding monitor that projects a beam across the drawer above the food (MiniMitter, Inc., Sun River, Oreg.). When the animal broke the infrared beam it caused a switch closure. An oscillator then sent off pulses (one pulse/second) and the total number of pulses indicated the length of time that the beam was broken which corresponds to the length of time spent feeding (recorded as feeding duration).

Cannulation and ICV administration were performed essentially as described in Murphy et al 1998 *Neuropeptides* 32:491–497, which is hereby incorporated by reference. After cannulation, rats were allowed to recover a minimum of seven days before injection with test compounds. All test substances were dissolved in artificial cerebral spinal fluid (aCSF). Rats were injected ICV with 1, 3, or 10 μg of rat NMU-23 (Phoenix Pharmaceuticals). Additional rats were injected ICV with either 0.3 or 0.03 μg of MT-II (Peninsula Laboratories) as a positive control for food intake suppression (melanocortin receptor agonist). One group of rats also had a radio transmitter placed in the peritoneal cavity for measurement of core body temperature and gross motor activity (MiniMitter, Inc., Sun River, Oreg.). Another group of ICV-cannulated rats were used in conditioned taste aversion (CTA) and sodium appetite (SA) aversion assays.

In the CTA study, rats were conditioned to two hour daily access to water, with access to water from two bottles for two hours each day for three days. On the fourth day, rats were given 0.15% saccharin for the two hour period instead of water and saccharin consumption measured. Rats were injected NMU-23 (0, 3, or 10 μg, ICV). LiCl was used as a positive control (0.15 M; 2 ml/kg, i.p.). On the fifth day, rats were given saccharin alone for the first hour, then water was added for the remaining 23 hours. Fluid consumption was measured at 1, 2, and 24 hours post injection. Aversion was assessed as a function of drinking preferences.

In the salt appetite assay, rats were given 0.5 M NaCl salt water to drink for three days along with food and regular water. After three days, two injections of furosemide (5 mg /0.2 ml, s.c.) were given at one hour apart to sodium-deplete the rats. Rats were then returned to salt-free water and given a sodium-deficient diet. Rats actively seek to defend their internal sodium levels. Consequently, when sodium is depleted, they will avidly drink salt solutions unless ill or nauseous. Twenty-four hours following furosemide administration, rats were given NMU (0, 3, or 10 μg, ICV), or LiCl (0.15 M, 2 ml/kg, i.p.) and given water and 0.5 M NaCl to drink. Fluid consumption was measured 1, 2, and 24 hours post dosing.

Results are shown in FIGS. 12A–F. All rodent studies described were conducted in accord with rules and guidelines of the Merck Research Laboratories Institutional Animal Care and Use Committee and the "Guidelines for the Care and Use of Laboratory Animals" [DHHS Publication No. (NIH) 85–23, revised 1985].

What is claimed is:

1. A method to identify compounds which modulate neuromedin U receptor 2 (NMUR2) activity comprising:
   (a) contacting the compound and a NMUR2 receptor as set forth in SEQ ID NO:2; and
   (b) determining if the activity of the NMUR2 receptor is modulated by measuring changes of intracellular calcium concentration.

* * * * *